United States Patent [19]

Zelin

[11] Patent Number: 4,819,752
[45] Date of Patent: Apr. 11, 1989

[54] BLOOD CONSTITUENT MEASURING DEVICE AND METHOD

[75] Inventor: Michael P. Zelin, Plainsboro, N.J.
[73] Assignee: Datascope Corp., Paramus, N.J.
[21] Appl. No.: 103,713
[22] Filed: Oct. 2, 1987
[51] Int. Cl.⁴ .............................................. A61B 5/00
[52] U.S. Cl. .................................... 128/633; 128/664; 250/252.1 R; 356/41
[58] Field of Search .................. 128/633, 664; 356/41, 356/411, 39; 250/252.1

[56] References Cited

U.S. PATENT DOCUMENTS

| | | | |
|---|---|---|---|
| 3,998,550 | 12/1976 | Konishi et al. | 356/411 X |
| 4,167,331 | 9/1979 | Nielsen | 356/41 X |
| 4,266,554 | 5/1981 | Hamaguri | 356/41 X |
| 4,407,290 | 10/1983 | Wilber | 356/41 X |
| 4,523,279 | 6/1985 | Sperinde et al. | 356/41 X |
| 4,621,643 | 11/1986 | New, Jr. et al. | 128/633 |

Primary Examiner—William E. Wayner
Attorney, Agent, or Firm—Fitzpatrick, Cella, Harper & Scinto

[57] ABSTRACT

A blood constituent measuring apparatus and method, which can be used to measure the oxygen (or other blood constituent) content of the blood. The apparatus includes sources of two or more wavelengths of light for transmitting, e.g., red and infrared light through a portion of the body, and a photodetector for generating respective signals representing each wavelength of light transmitted through the body portion. The photodetector signals have pulsatile and non-pulsatile components. The oxygen content of the blood is computed based on the light transmitted through the body portion at each wavelength, as determined from the pulsatile component, amplified alone after the much larger non-pulsatile component is subtracted from it. The apparatus can compute the oxygen content of patients with weak pulses, or unstable physiological states, or both, by using, preferably, a plurality of independently settable gains, to maintain the signal level within a range suitable for accurate measurement. In addition, the apparatus preferably compensates for drift in the non-pulsatile component which can be caused when the patient's blood pressure, for example, becomes erratic, thereby increasing the accuracy of its computation of the oxygen content of the blood. To the extent possible, the signals produced for the different wavelengths are time-multiplexed onto a single channel. A test mode is preferably provided, in which only one wavelength of radiation is produced, resulting in a computation equal to what would be obtained in normal operation if the amounts of sensed radiation were the same for all wavelengths.

60 Claims, 7 Drawing Sheets

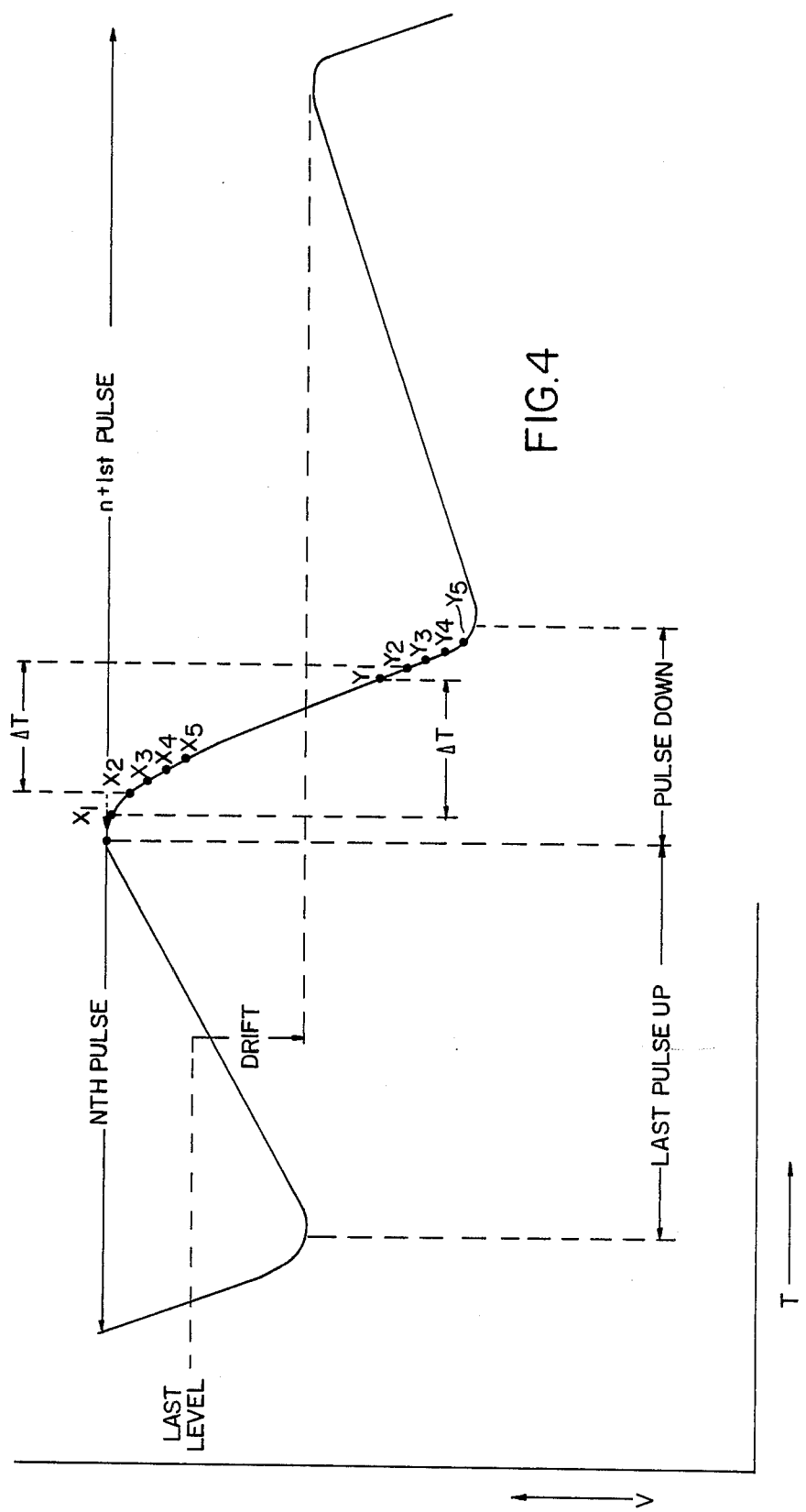

BLOOD CONSTITUENT MEASURING DEVICE AND METHOD

BACKGROUND OF THE INVENTION

1. Field of the Invention

The invention relates to a blood constituent measuring device and method, and more particularly relates to a non-invasive device and method for determining the concentration of oxygen in the blood.

2. Description of Pertinent Background Information

The well-known explosion in electronics technology over the past few decades has found many diverse areas of application. On such area is the monitoring of physiological functions. The present invention relates to such monitoring, and specifically, to the measurement of tissue oxygenation.

Monitoring oxygenation levels is desirable in the more critical areas of the hospital, espcially when a patient is being ventilated by machine. There is potential for mishap, both physiological and mechanical. Foremost examples are patients under anesthesia in the operating room, and patients in intensive/critical care units.

Two forms of electronic monitoring have gained widespread acceptance for the monitoring of oxygenation—transcutaneous monitoring of the partial pressure of oxygen, and optical monitoring of the percent hemoglobin saturation (oximetry).

Transcutaneous monitoring seeks to measure directly the partial pressure of oxygen in the tissues by measuring the oxygen which diffuses through a locally heated area of the skin. An implicit assumption of transcutaneous monitoring is good correlation between the partial pressure of diffused oxygen and the partial pressure of oxygen in the tissues. Thick and fatty skin is the Achilles' heel of this approach.

Oximetry seeks to determine the percentage of available hemoglobin in the red blood cells carrying oxygen to the tissues from the lungs. This percentage is related to the partial pressure of oxygen in the blood by the well established oxygen-disassociation curve. The higher the partial pressure, the greater is the diffusion of oxygen from the capillaries to the tissues. Thus, although oxygen saturation is not a direct measurement of the degree of tissue oxygenation, unless the cardiac output (rate at which the heart pumps blood to the body) is impaired, the two measurements will be strongly correlated.

The oximetry measurement is optical—it essentially measures how red the blood is. As most are aware from common experience, oxyhemoglobin (hemoglobin bound with oxygen) is "redder" than hemoglobin.

The method employed in such measurements is spectrophotometry. Spectrophotometry can determine the relative concentrations of N substances in a mixture by measuring the absorption by the mixture of N wavelengths of light, if the absorptions by the individual substances are sufficiently different. Mathematically, the approach amounts to solving N equations in N variables.

In the blood, hemoglobin and oxyhemoglobin are the primary substances which absorb light in the red and near-infrared region of the spectrum. Thus, two wavelengths of light (typically one red and one near-infrared are employed for maximum discrimination) are required to measure the percentage saturation (oxyhemoglobin as a percentage of total hemoglobin and oxyhemoglobin).

In vitro devices (whose use requires drawing a blood sample for measurement external to the body) have existed for a number of years. More recently, in vivo devices (which perform the measurement in blood in the body) have appeared, but these were invasive, requiring a fiber optic tube to be inserted into the bloodstream. Making a practical non-invasive device which could continuously monitor percent saturation did not await only the electronics revolution, however. There were other practical difficulties, for it is the percent saturation of the arterial blood which correlates to tissue oxygenation, and one aspect of the problem, therefore, is how to measure, non-invasively, the absorption of the arterial blood and exclude the contributions by venous blood, bone, skin, etc. One approach by Wood in the 1940's was to squeeze the earlobe to get a reading of the absorption of everything but blood, and then heat the ear to arterialize the blood which entered when the pressure was taken off. In the 1970's, Hewlett-Packard marketed a device which used eight wavelengths of light in an attempt to account for contributions from the non-blood portions of the earlobe. Use of that device also involved heating the ear to arterialize the blood. Neither of these devices were suitable for use in the operation room or intensive/critical care units: they were too large, expensive and complicated to use.

Newer devices, which are gaining widespread acceptance, are of a type called "pulse oximeters". The principle upon which they are based is simple. The light transmitted through the monitoring site (typically the finger, ear or toe), has a pulsatile component related to the extra blood pumped into the arterial vessels of the monitoring site with each heartbeat. This extra blood is arterial. Therefore, analysis of the pulsatile signal yields the percentage oxygen saturation of the arterial blood.

There is another complication related to the in vivo measurement. Strictly speaking, spectrophotometric analysis is based upon a model wiich includes pure collimated light, the intensity of which is reduced only by aborption by the mixture to be analyzed. The intensity is reduced by an exponential process known as "Beer's Law". Calculations used in in vivo measurement assume this exponential process. In non-invasive pulsatile oximetry, the light is diffused by the tissues being analyzed and the pulsatile signal received is due to scattering by the red blood cells as well as absorption by the hemoglobin and oxyhemoglobin molecules in the arterial vessels.

Fortuitously, it is found that if a "Beer's Law" type relationship is assumed, the coefficients which determine the exponential characteristic can be determined experimentally by measurement over a population of patients. Since a scattering process is involved as well as an absorption process, the coefficients are larger, and yet they are consistent enough over a population to be the basis of a useful device.

Such devices are described in U.S. Pat. Nos. 3,998,550, 4,266,554, 4,407,290 and 4,621,643. All are pulsatile oximeters and differ only by the means in whichthe signals are processed. The device of U.S. Pat. No. 3,998,550 solves the exponential Beer's Law equations by using a logarihmic circuit, while that of U.S. Pat. No. 4,266,554 takes the derivative. U.S. Pat. No. 4,407,290 recognizes that the pulse is sufficiently small to allow linerization of the equations, thus obviating the need to solve exponential equations.

While the above patents illustrate the basic principles upon which pulse oximetry is founded, and are directed to devices which are based upon these principles, all of them fail to focus upon some of the specific difficulties associated with the use of such devices in practice. It is important to recognize that these devices are typically utilized to monitor patients who are not healthy. Thus, these devices must operate under conditions of unstable physiological states and on patients who may have very weak pulses. In addition, these devices must operate from monitoring sites which exhibit a wide variation in light transmission properties.

SUMMARY OF THE INVENTION

It is an object of the present invention to provde a non-invasive oximeter capable of accurately measuring the percent oxygen saturation of arterial blood in a wide variety of patients, including patients who have very weak pulses and/or unstable physiological states.

It is another object of this invention to provide a non-invasive oximeter which will operate successfully in the presence of great amounts of electrical noise such as is generated by an electrosurgical unit (ESU) as is typically used in the operating room.

It is a further object of this invention to provide an oximeter which minimizes the number of electronic circuits required, thus making the instrument less expensive and more reliable.

It is yet a further object of this invention to provide a means for the user of any non-invasive oximeter (such as those to which U.S. Pat. No. 3,998,550, 4,266,554, 4,407,290 and 4,621,643 are directed) to perform a complete functional test of the entire system while the sensor probe is attached to the patient, thus allowing the user to have full confidence in the operation of the monitor at any time.

There is a need for a pulsatile oximeter which meets these objects.

The present invention, as do the devices of the referenced patents, comprises means for sensing electromagnetic energy of at least two wavelengths as it passes through a portion of a patient's body, processes the signals so produced so as to separate out a pulsatile portion of each signal which is related to the physiological pulse, and then determines the percent saturation as a function of the relative sizes of the pulsatile and non-pulsatile components.

According to one aspect of the present invention, in processing the signals to separate out the pulsatile component, a number of discrete gains are used to compensate for variations in the total amount of electromagnetic energy received due to variation in the strength of the emitting source, the thickness of the portion of the body through which the electromagnetic energy is being sent, and placement of the detector of energy with respect to the emitters. A digital-to-analog converter is provided to allow variable amounts of voltage to be subtracted off these signals, and another series of discrete gains are applied to the residual signal, which is primarily composed of the pulsatile signal, to allow variable pulse strengths (i.e., weak or strong) to be digitized for analysis by a microprocessor subsystem. This structure enables the unit to respond to changes in signal sizes essentially instantaneously—that is, without having to skip the processing of any pulses.

In addition, it is another aspect of the invention to recognize that the non-pulsatile portion of the signal is not constant, but is a function of the total amount of blood in the area being monitored, and thus physiological changes (e.g., in the mean blood pressure) can cause it to vary. If this is not taken into account, the measurement of the size of the pulsatile component will be affected, as a portion of its measured size is related to this "drift" in the non-pulsatile portion. Accordingly, the processing and computing means preferably comprises means for recognizing this component of the received signal, and calculating the value of the pulsatile component in a manner which compensates for it.

According to still another aspect of the invention, the processing of the signals from the multiple wavelengths is multiplexed onto a single channel to the extent possible, to reduce the number of components. The only part of the procesing performed in parallel is the filtering which is performed to reject large interfering noise sources such as produced by an ESU unit.

Although this invention finds its most important application as a pulsatile oximeter for measuring the level of arterial oxygen saturation, the basic structure disclosed can be used to measure the relative concentration of any number of constituents of any pulsatile cavity, provided the electromagnetic absorption characteristics of such constituents are suitably related to one another.

The user-initiated calibration or testing described in the detailed description can be added to any of the devices described in the referenced patents.

The present invention differs from the previous systems, inter alia, in the way in which it processes the signals, both in relation to separating out the pulsatile component, determining the size of the pulsatile component and determining the size of the non-pulsatile component.

BRIEF DESCRIPTION OF THE DRAWINGS

The invention will now be described with reference to the detailed description which follows in conjunction with the attached drawings, in which:

FIG. 4 is a schematic illustration of the drift compensation of the present invention.

DETAILED DESCRIPTION OF THE PREFERRED EMBODIMENT

The detailed description of the invention is divided into three sections. The first describes the structure of the preferred embodiment of the device, with reference to the block diagram of FIG. 1. The second describes how the illustrated structure enables the oximeter of the invention to operate on a greater variety of patients, with a wider range of pulse strengths, than is possible with conventional devices, and how, therefore, the present invention is a more practical device. The third describes how the processing of the signals increases the accuracy of the measurement of percent saturation, as compared with that obtained with previous devices.

Structure of the Preferred Embodiment

Figure 1:
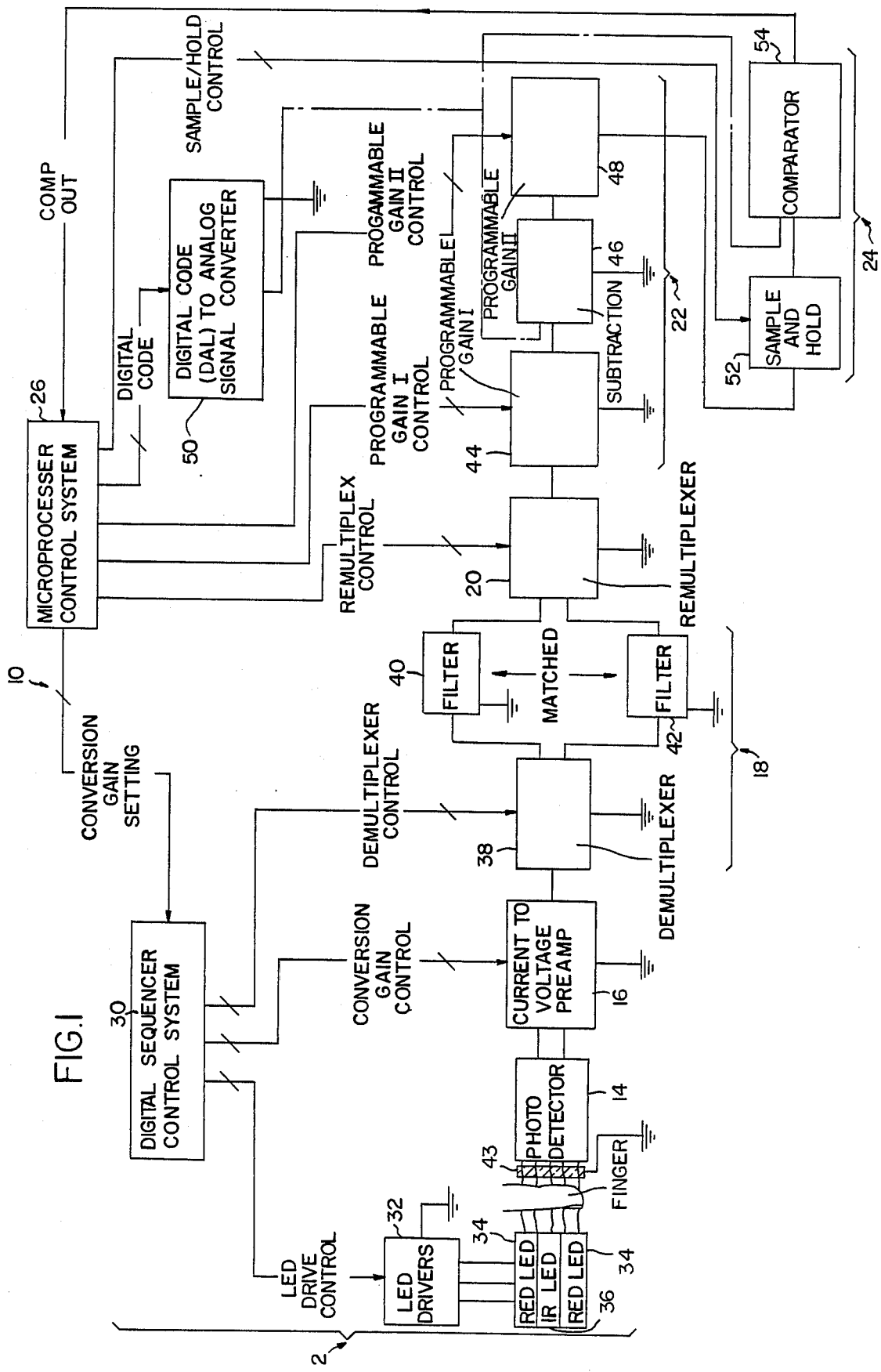
FIG. 1 is a block diagram of the oximeter of the present invention.
Figure 1A:
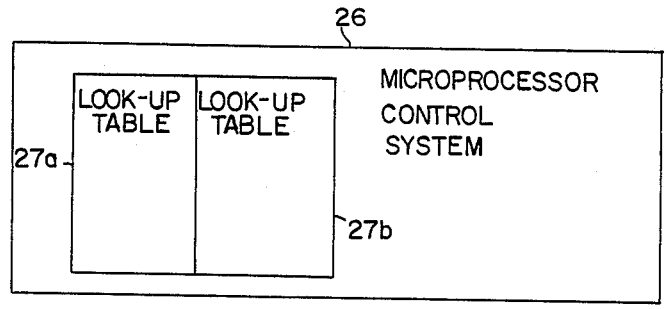
FIG. 1a is a schematic illustration showing a detail of the microprocessor control unit shown in FIG. 1.

FIG. 1 illustrates an oximeter generally referred to by reference numeral 10. It should be noted that, although the embodiment of the present invention described herein is a device for measuring the oxygen content of the blood, it is within the scope of the present invention to measure the concentration of other blood constituents.

Oximeter 10 comprises a light emitting section 12, a light sensing section comprising a photodetector 14, a signal converting section including a current-to-voltage preamp 16, a demultiplexing and filtering section 18, a remultiplexing section 20, a gain and subtraction section 22, a digitizing section 24, and a processing, computing, and display section comprising a microprocessor subsystem control system 26, which also assists digitizing section 24.

Light emitting section 12 comprises a digital Sequencer control device 30 for controlling LED drivers 32 which alternately drive two red LED's 34 and an infrared LED 36 at a 2.5 kHz rate to produce alternating red and infrared pulses having well-defined pulse widths. Sequencer 30 is actuated by microprocessor subsystem 26.

Sequencer 30 alternately pulses the LED's so that the circuitry detecting and processing the light transmitted through a portion of the patient's body can discriminate the photodetector's response to red light from its response to infrared light.

Although a finger is illustrated in FIG. 1 as the portion of the body through which light is transmitted and measured, and the following description is in terms of a finger, it is to be understood that the preferred embodiment can be used to calculate the oxygen saturation of the blood by transmitting light through other portions of the body, such as an ear lobe, a toe, etc.

A finite-state machine (implemented in the preferred embodiment by digital sequencer 30), rather than microprocessor subsystem 26, provides the immediate control for the LED drive 32. This is because timing signals from a microprocessor subsystem cannot be generated as precisely as with a digital sequencer. Output signals from digital sequencers are externally latched to the devices to be controlled (such as the LED's) at precise intervals defined by a single clock signal. Sharp, well defined red and infrared pulses are generated by the red and infrared LED's under control of the digital sequencer 30. If controlled directly by the microprocessor subsystem 26, the pulse widths and times would exhibit much greater amounts of jitter noise. The digital sequencer 30 also controls a demultiplexer 38, as is dicsussed below.

Figure 2A:
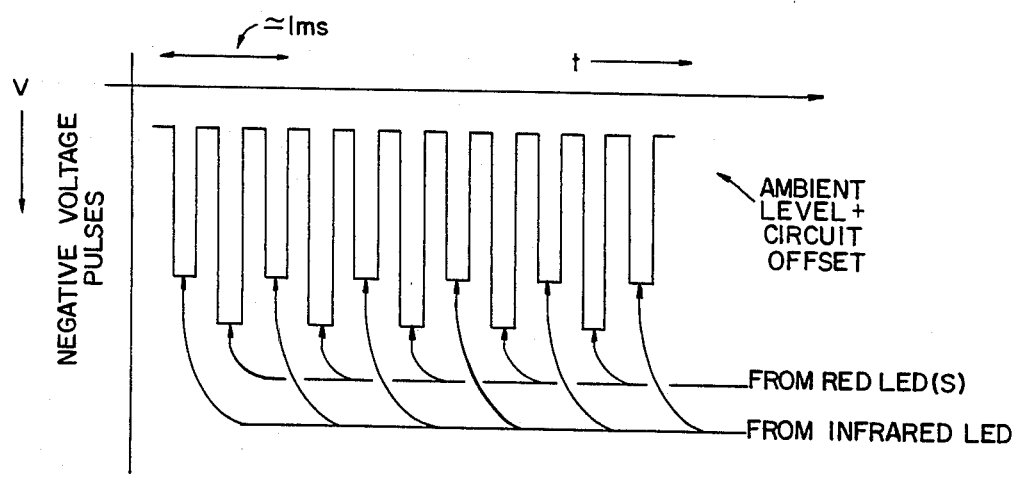
FIG. 2a illustrates the voltage waveform output from the detector preamplifier, as the latter responds to red and infrared LED pulses.

LED's 34 and 36 are positioned on one side of the patient s finger. A single photodetector 14 is positioned on the other side of the finger to detect the light, both red and infrared, transmitted through the finger and to produce an electrical signal proportional to the amount of light received. Because LED's 34 and 36 are driven by sequencer 30 in such a manner as to produce alternating pulses of red and infrared light, odd-numbered pulses produced by photodetector 14 carry information about the finger's absorption of red light, and the even-numbered pulses carry information about the finger's absorption of infrared light (see FIG. 2a). Use of a single photodetector to sense both the red and the infrared light further guarantees that the detected light of both wavelengths has passed light through the same portion of the finger. This ensures that the two signals produced by processing the response to the red and the infrared light are correlated, in the sense that variations between them are related to the different characteristic attenuations of red and infrared light by a single group of tissues and are not due to the two wavelengths of light passing through two different groups of tissues.

To ensure still further that the signals produced by processing the response to the red light and to the infrared light are correlated, two red LED's 34, instead of only one, can be used. The two red LED's are on either side of the single infrared LED 36 and are operated in unison. Thus, there is a plane of symmetry in the illumination pattern.

The photodetector 14 produces an electrical signal in the form of a current. A current-to-voltage preamp 16 converts the current signal to a voltage signal. The amount of light impinging upon the photodetector, and therefore the magnitude of the current signal, is a function of the width of the part of the body chosen for examination. Since these can vary widely, it is another function of the preamp 16 to compensate coarsely for the intensity of light reaching the photodetector 14. This is accomplished by designing the preamp 16 to have several, e.g., three, different transimpedance (current-to-voltage) gains. These gains are controlled by the finite-state machine implemented by the digital sequencer 30 and can preferably be chosen independently for the red and the infrared pulses. In addition, a gain of zero can be chosen, to permit calibration of the system as described below at the end of the section entitled "Structure of the Preferred Embodiment". The appropriate gains are transmitted to the digital sequencer from the microprocessor subsystem 26.

The signals output from preamp 16 are multiplexed signals in which signals representing the transmission of red light through the finger alternate in time with signals representing the transmission of infrared light through the finger. This multiplexed signal is now demultiplexed to filter the red and the infrared signals separately. This is done because, in order for the filters adequately to reduce high frequency noise components, the time constant of the filters must be substantially longer than the multiplexing rate. If sent through a single filter with this longer time constant, the information inherent in the red signal would be mixed with that from the infrared signal, thus corrupting the measurement. In order to filter these signals separately, the output from preamp 16 is demultiplexed by a demultiplexer 38. Demultiplexer 38 produces two separate signals, one representing red light transmitted through the finger and one representing the infrared light so transmitted. The two signals are transmitted through two parallel, frequency-matched low pass filters 40 and 42. Frequency matching ensures that the shape of the physiological signals passing through the two filters is processed in substantially the same manner.

These signals are generated by the demultiplexer in the following way. During the period of time that the multiplexed signal from photodetector 14 represents tranmission of red light, the signal is switched into the channel with the low pass filter 40, and during the period of time that the multiplexed signal from photodetector 14 represents transmission of infrared light, the signal is switched into the channel with the low pass filter 42, A portion of the signal being switched into the low pass filters 40 and 42 is an offset signal not associated with transmission of light fom LED's 34 and 36 through the finger. This includes ambient light falling on the photodetector 14 and electronic offset voltags generated by the photodetector 14, preamp 16 and demultiplexer 38 (see FIG. 2a). The demultiplexer causes this portion of the signal to be subtracted, by creating a signal which is the negative of the multiplexed signal (i.e., by amplifying by −1) from photodetector 14 and switching it into both the filters 40 and 42 during the portions of time that none of the LED's 34 and 36 are transmitting light (i.e., in between the red and infrared pulses). During these portions of time this signal is the exact negative of the offset signal. Thus, if the negative signal is switched into the two filters 40 and 42 for a period of time equal in duration to the period of time when the signal from photodetector 14 is switched into the filters 40 and 42, the averaging effect of the low pass filters will cause the offset signal to be exactly cancelled out.

Demultiplexer 38 is controlled by digital sequencer 30 so that the process of demultiplexing is synchronous with the alternating pulses of red and infrared light, their generation being controlled by the digital sequencer 30 as well.

The sequence of events controlled by the finite-state machine can be altered to allow the function of the entire instrument to be tested in actual operation (as opposed to a "bench test" of the electronics, in the factory, for example). A control signal from the microprocessor subsystem 26 alerts the finite-state machine implemented by the digital sequencer 30 to pulse only the infrared LED, both during the time when the red LED or LED's would be pulsed and when the infrared LED would normally be pulsed. Thus, in this testing mode, the two signals demultiplexed into the filters 40 and 42 are identical. If the machine is functioning correctly, it should therefore yield durinq this test the same result for percent oxyqen saturation (e.g., 84 percent) which is indicated when the modulation of the red and infrared light transmission is identical under normal operation. Note that the same process can be repeated with only the red LED or LED's being pulsed. Thus, a test of every element in the system can be initiated by the user via an external control, at any time, on every patient.

This aspect of the invention can be used in any pulsatile oximeter in which radiation of two or more wavelengths emitted seriatim through the portion of the body being monitored and the level of the transmission of which through the body is monitored by a single detector element (which currently includes all pulsatile oximeters known to the present inventor). The only requirement for this is that the signals which control the LED's be distinct from those which control the demultiplexing of the signals into the parallel processing channels.

It should be noted that one of the most important noise sources that the filters reduce is the use of an electrosurgical instrument in the operating room. In order to reduce this potential interference even further, a grounded translucent conductive window (43) is preferably placed between photodetector 14 and the finger to prevent interfering current from passing through the electrosurgical unit, through the finger to photodetector 14 and into the current-voltage preamp 16.

Figure 2B:
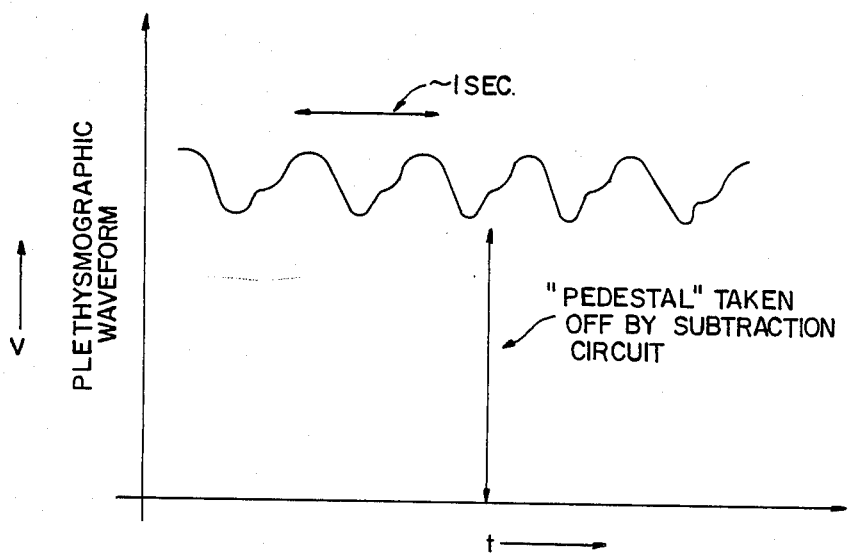
FIG. 2b illustrates the voltage waveform from one of the red or infrared filters, in which the physiological pulsatile and non-pulsatile components are shown.

An illustration of one of the red and infrared waveforms after the demultiplexed LED pulse signal is transmitted through the low pass filters is shown in FIG. 2b. This waveform, called a plethysmographic waveform, has a pulsatile nature which should be noted. These pulses represent the rising and falling in the intensity of the light transmitted through the finger. The intensity of light transmitted through the body is a function of the amount of blood the light encounters as it passes through. The amount of blood varies with the heartbeat of the patient. Each time the heart pulses arterial blood through the blood vessels of the finger, the amount of blood increases, reducing the amount of transmitted light. As the blood vessels relax between heartbeats, the amount of blood is reduced and the amount of light transmitted through the finger returns to its previous level. The electronic instrumentation discussed below processes this varying portion of the photodetector's output, which is therefore sensitive only to the attenuation properties of arterial blood and not to other portions of the finger, such as skin, bones, venous blood, etc.

It should be noted that if the sensor probe is designed correctly, such that the red and the infrared light pass through substantially the same tissue, the pulses in the plethysmographic waveform in the red channel will be shaped identically to those in the infrared channel. Only their size and the slowly-varying voltage on which they sit will be different.

As mentioned above, it is one of the objects of this invention to reduce the amount of hardware needed to process the signals, thus making the overall device as simple, inexpensive and reliable as possible. This object is furthered by providing a remultiplexer 20 connected to the outputs of filters 40 and 42. Remultiplexer 20 time-multiplexes the filer outputs onto a single processing channel. All further processing is performed in a single channel. Contrast this with, for example, the device of U.S. Pat. No. 4,407,290, in which processing is performed in two parallel hardware channels until the signals are ultimately digitized for analysis by the software.

Remultiplexer 20 preferably operates at a 240 Hz rate so as to sample the two channels and the two plethyscographic waveforms at a 120 Hz rate. This rate ensures adequate resolution of the high-frequency protions of the waveform.

The gains applied to the remultiplexed signal will now be described.

After being remultiplexed, the signals are transmitted to gain and subtraction section 22 where the signals are amplified by a first programmable microprocessor subsystem controlled gain 44. A portion of the signals is then subtracted by a subtraction circuit 46 under the control of microprocessor subsystem 26, and the remaining portion of each signal is then amplified by a second programmable microprocessor subsystem controlled gain 48.

Figure 3A:
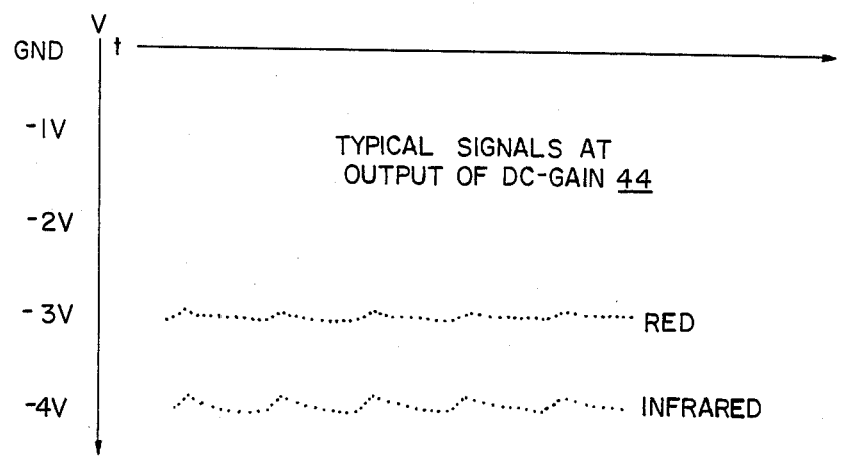
FIG. 3a is a graphical representation of the red and infrared waveforms after these waveforms have been filtered and amplified.

The signals are shown in FIG. 3a as a series of dots to indicate that they are multiplexed into a single channel. If that figure were drawn on as expanded time scale, it would be apparent that the signal alternates between the two plethysmographic waveforms at the 240 Hz multiplexing rate. It should be understood that all subsequent processing of the remultiplexed signal is actually a hybrid of two independent signal processing procedures. All gains and voltage subtractions to be described are chosen independently for the red and the infrared signals and as such are changed back and forth at the 240 Hz multiplex rate.

Gain 44 independently amplifies the red and infrared portions of the remultiplexed signal by one of several gains, in the preferred embodiment: 1, 2, or 4. The ability of gain 44 to apply one of three discrete gains to the remultiplexed signal allows the red and infrared signals to be maintained within a range that enables them to be digitized with a resolution of at least eight bits. Further, it should be noted that because preamp 16 also amplifies the signal by one of several (again, preferably three) discrete gains, nine (if the number of values assumable by gain 44 is three for each channel) possible discrete gains can be applied independently to the red and the infrared signals. This permits oximeter 10 to measure the oxygen content of patients having a wide range of finger thicknesses. A more complete description of this aspect of the system is presented below in the section entitled "Advantages of Structure of the Preferred Embodiment".

Figure 3B:
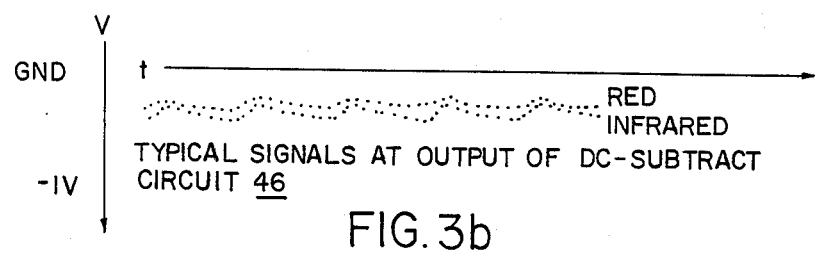
FIG. 3b is a graphical representation of the red and infrared waveforms at a time later than that illustrated in FIG. 3a, after a portion of the non-pulsatile component of these waveforms has been subtracted.
Figure 3C:
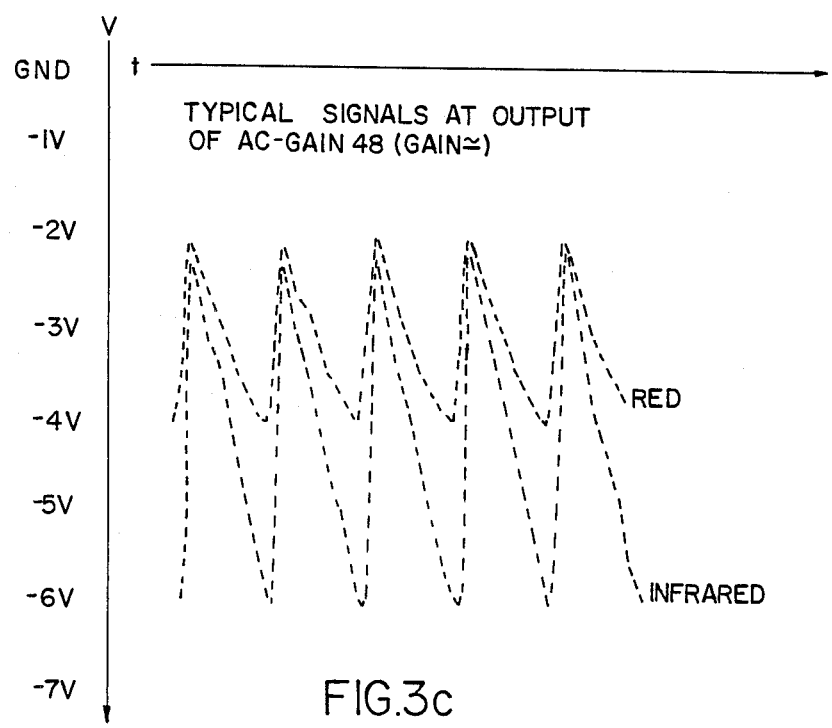
FIG. 3c is a graphical representation of the red and infrared waveforms at a time later than that illustrated in FIG. 3b, after the red and infrared waveforms, absent a large portion of the non-pulsatile component, have been amplified.

After being amplified by gain 44, a large portion of the non pulsatile component is subtracted off by the subtraction circuit 46. The voltage subtracted off is generated by digital-to-analog converter (DAC) 50 with the digital code being supplied by microprocessor subsystem 26. The manner in which this code is chosen is also described in the section entitled "Advantages of Structure". The value of the code is stored by the microprocessor subsystem for use in later calculation. As shown in FIG. 3b, the amount subtracted off is selected so as to leave a small component of non pulsatile signal. This is to ensure that the complete pulsatile component is retained for further processing.

After subtraction of a portion of the non-pulsatile component, the remaining red and infrared signals are amplified by gain 48. Gain 48 amplifies the pulsatile component of the signal by one of several distinct gains, preferably 5, 22.4, or 100. Because a majority of the non-pulsatile component has been subtracted from the signal, gain 48 is able to amplify the pulsatile component sufficiently so that even very weak pulses yield information on the percentage of oxygen saturation of the blood, while still keeping the amplified signal within the sensitivity range of the digitizing circuitry which follows. As a result, if, during surgery, the patient's pulse becomes very weak due to difficulties in the functioning of the heart, for example, the anesthesiologist can still obtain an accurate value for the oxygen saturation of the blood with the present invention. This is illustrated in the section entitled "Advantages of Structure".

After amplification of the signal by gain 48, digitization section 24 digitizes the signal, which is transmitted to the microprocessor subsystem for processing. Digitization section 24 comprises a sample-and-hold circuit 52, a comparator 54, and DAC 50. Digitization is performed under microprocessor subsystem control of DAC 50 in conjunction with sample and hold circuit 52 and comparator 50. Microprocessor subsystem 26 actuates DAC 50 to send an analog signal to comparator 54. Comparator 54 compares this signal from DAC 50 with the subtracted and amplified pulsatile red or infrared signal outputted from sample and hold circuit 52. If the voltage of the signal generated by DAC 50 is less than that of the signal from sample-and-hold circuit 52, the output of comparator 54 actuates microprocessor subsystem 26 to instruct DAC 50 to increase the voltage of its output, whereas if the voltage of the signal generated by DAC 50 has a voltage less than that generated by sample and hold circuit 52, the output comparator 54 indicates to microprocessor subsystem 26 to instruct DAC 50 to decrease the voltage of its output. This process of successive approximations continues until DAC 50 produces substantially the same voltage signal as that output by sample-and-hold circuit 52. When this occurs microprocessor subsystem 26 produces a digital representation of the voltage of the signal outputted by sample-and-hold circuit 52 to a resolution of twelve bits. As a result, oximeter 10 can digitize and discriminate changes in the voltage of the pulsatile component lower than 0.1% of the total signal.

Figure 2C:
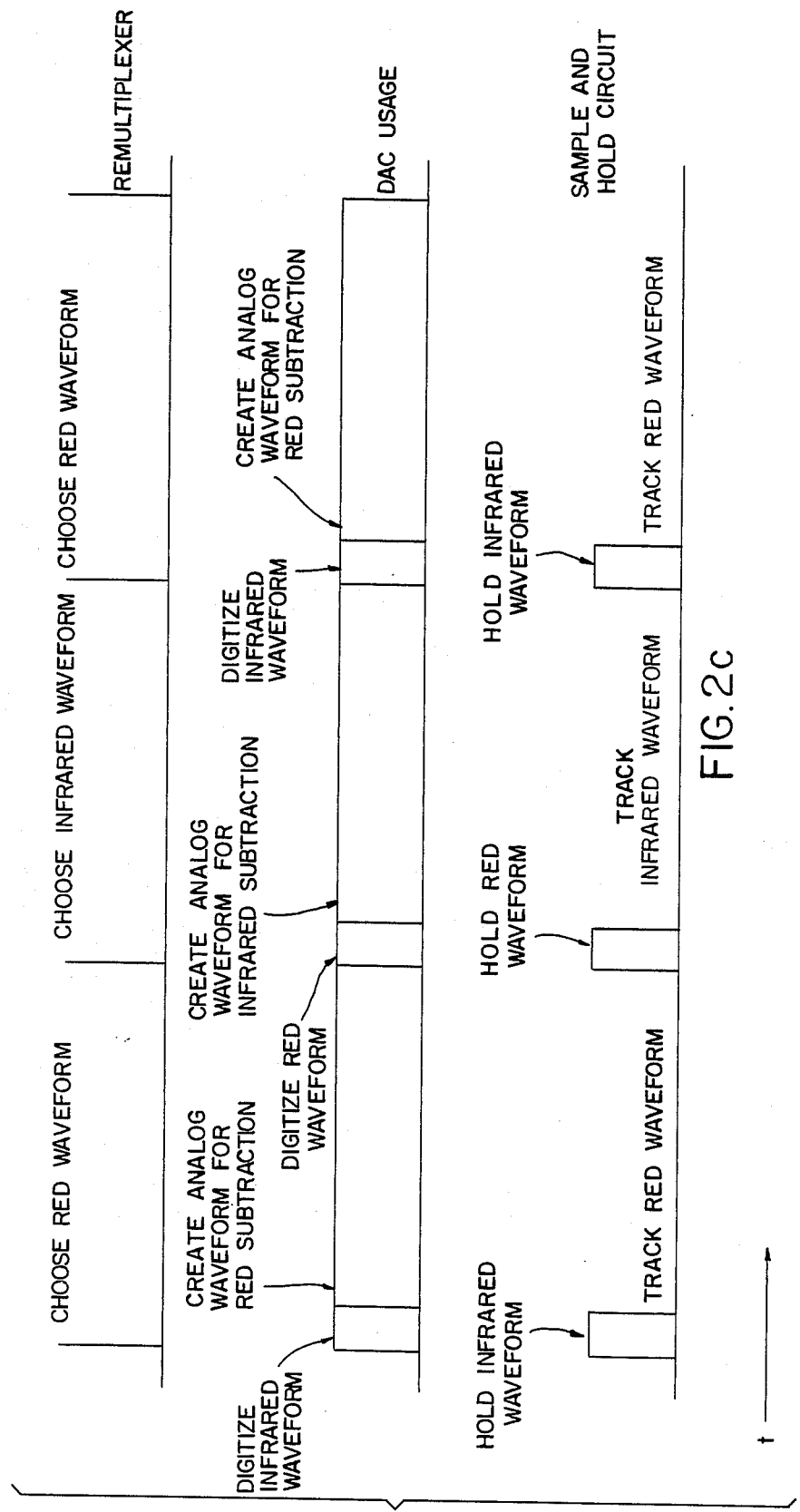
FIG. 2c is a schematic view of the operation of the remultiplexer control, the digital-to-analog converter, and the sample-and-hold circuit.

DAC 50, therefore, performs two functions: it subtracts a portion of the non-pulsatile component and it assists in digitizing the remaining pulsatile component. Using the DAC to perform these two functions reduces the amount of hardware needed to process the signals. Remultiplexer 20, DAC 50, and sample-and-hold circuit 52 function together so that DAC 50 can both subtract and assist in digitizing the electrical signals as illustrated in FIG. 2c. More specifically, every 1/240th of a second the control functions of device 10 are changed to process the red or the infrared portion of the signal. For example, every 1/240th of a second remultiplexer 20 switches from sampling the red portion of the signals to sampling the infrared portions of the signals, or vice versa, as illustrated at the top of FIG. 2c. In addition, every 1/240th of a second the amount of amplification provided to the signal by preamp 16, gain 44, and gain 48 and the digital input code transmitted to DAC 50 for use in the subtraction circuit 46, is changed from the values associated with the red waveform to the values associated with the infrared waveform, or vice-versa, under the control of the microprocessor subsystem so that the red and infrared portions of the signals are independently amplified as needed.

As illustrated in the middle portion of FIG. 2c, during the beginning of the 1/240th of a second during which remultiplexer chooses the red waveform to be further processed, DAC 50 participates in digitizing the infrared waveform that immediately preceded the red waveform now being sampled. This is accomplished relatively quickly so that during the vast majority of the 1/240th of a second during which remultiplexer 20 samples the red waveform, DAC 50 subtracts a large portion of the non-pulsatile component of the red waveform, leaving the pulsatile component of the red waveform and a small non-pulsatile buffer. At the beginning of the next 1/240th of a second, the substantial red waveform, which has settled to its new value, is captured by sample-and-hold circuit 52, as illustrated at the bottom of FIG. 2c. DAC 50 is now available to be used in digitizing this subtracted red waveform.

Once the subtracted signals are digitized they are stored in the memory of microprocessor subsystem 26, which computes the oxygen saturation of the blood as a function of the digitized, subtracted, and amplified pulsatile component of the signals and as a function of the stored subtracted portion of the non pulsatile component of the signals, as is described below, in the section entitled "Processing of the Signals by the Microprocessor Subsystem".

As previously mentioned, the preamp 16 can be made to have a gain of zero to allow offsets in the circuitry to be calibrated out. This calibration process is now described.

The calibration occurs when the unit is first turned on before any signals are processed. Offsets determined by the calibration are stored in the microprocessor subsystem's memory for access by the microprocessor subsystem when processing the signals during normal operation.

Offsets are introduced by the standard signal processing components which are used to implement the functional blocks described above. The offsets will be a function of the gain settings 44 and 48. In addition the offsets will be different for the processing of the red signal and the processing of the infrared signal since the red signal is processed by filter 40 and the infrared signal is processed by filter 42. Thus the microprocessor subsystem must determine and store offsets for all 18 combinations of gain 44, gain 48 and channel (red vs. infrared).

The offsets are determined in pairs. A pair consists of $V_{offset-subtract}$ and $V_{offset-digitize}$. $V_{offset-subtract}$ is used to modify the value of $V_{subtract}$ in calculations by the microprocessor subsystem, and $V_{offset-digitize}$ is used to modify the value of $V_{digitize}$ in these calculations.

When the preamp current is shorted to ground, currents generated by the photodetector in response to light do not generate voltage signals for further processing. Thus ideally, if no offsets were generated by the signal processing components, the digitizing section 24 should sense zero voltage when DAC 50 is set by code generated by the microprocessor subsystem 26 to subtract off zero volts after amplifier gain 44. The offset pair $V_{offset-subtract}$ and $V_{offset-digitize}$ represent the deviation from this ideal situation. $V_{offset-digitize}$ represents the voltage digitized when $V_{offset-subtract}$ is subtracted from the signal at the output of gain 44 by DAC 50.

The offsets are measured via a successive approximation approach similar to the approach previously described used to perform digitization. The microprocessor subsystem 26 alternatively increments and decrements the code it sends to the DAC 50 for subtraction off of the voltage output by gain 44, until it reaches a code which results in a suitably small voltage signal being input to the digitizer 24 (less than 1 volt). Since the DAC 50 can only generate discrete voltages (1 of 4096 values for a 12-bit DAC), a code which could generate a voltage at the input to the digitizer much closer to zero volts may not exist.

The code at the input to the DAC which generates the subtraction voltage is then stored as $V_{offset-subtract}$ and the resulting digitized code is stored as $V_{offset-digitize}$.

Advantages of the Structure of the Preferred Embodiment

One of the objects of the invention is to allow the oximeter to be used on a wide variety of patients under a great variety of conditions. How this is achieved can be better understood by referring to the plethysmographic signal in FIG. 2b. The height of the total signal level corresponds to the amount of light which is transmitte through the finger (or other body part) and is thus a function of the thickness of the finger. For an oximeter designed to operate upon both fingers and ears, for example, the amount of light coming through can vary by a factor of more than 100. The percentage modulation (ratio of the size of the plethysmographic pulse to the total signal level) is a function of the strength of the patient's pulse: the stronger the pulse, the more extra blood will be pumped into the blood vessels during the heart beat, and therefore the greater will be the percentage modulation. This can also vary greatly among patients.

Processing the signals from such a wide range of signal levels is accomplished by choosing the appropriate values for gains 16, 44 and 48 in the signal processing circuitry. Tables 1, 2 and 3 and the following description indicate how these gain settings are chosen for varous signal sizes.

To measure the percent saturation accurately, the full height of the pulsatile component should usually be at least approximately fifty times as large as the resolution of the digitizing system. (At higher saturation levels, where the accuracy of the computation of %SaO2 is less. sensitive to errors in measuring the plethysmagraphic signal, the height can be as small as about twenty-five times the resolution of the digitizing system). To try and be sure that such a ratio is achieved, the gains 16, 44 and 48 are preferably chosen to maintain the height of the pulsatile component one-hundred times as large as the resolution of the digitizing subsystem 24.

In addition, however, the pulse height should be no more than one third to one-fourth the full scale range of the digitizing subsystem. This is because drifts in the total signal level (discussed in more detail in the next section, "Processing of Signals by the Microprocessor Subsystem") tend to push the pulsatile signal out of the digitizing range. By maintaining the pulse height as a small fraction of the full range, the oximeter has more time to react in order to maintain the signal within the range of the digitization subsystem 24 by changing the voltage substracted off by the DAC 50.

For an eight-volt full scale range of a twelve-bit digitizing subsystem, corresponding approximately to a two-millivolt resolution, the device should preferably maintain the pulsa-height within a range of from 200 millivolts to between 2 and 2.5 volts.

Tables 1 and 2 indicate how the gains 16 and 44 maintain the output of gain 44 between 2 volts and 5 volts for detector current signal levels between 0.25 microamp (very thick finger and dim LED) and 40 microamps (very thin finger and bright LED). Thus, if the pulsatile component modulates the total signal between 0.1% (very weak pulse) and 10% (very strong pulse), gain 48 can be chosen to maintain a pulsatile height between 200 mullivolts and 2.5 volts (see Table 3).

It should noted that the oximeter can operate on patients who produce signals outside these preferable ranges, because as discussed above, the operating ranges described are not absolute physical limits. Also, the range limits described in Tables 1, 2 and 3 are for worst case combinations of total signal current level and modulation levels. For example, a pulse much smaller than 0.1% modulation can easily be measured if the total current signal produced by the detector is much greater than 0.25 microamp. The tables indicate the advantage of using multiple gain settings for greatly expanding the operating range of a pulsatile oximeter, which is important in a practical device.

The use of gain-changing circuitry is a significant improvement over the prior art. The devices shown in previous patents such as the four referred to above maintain a single fixed gain for either the plethysmographic portion of the signal, or both that portion and the entire signal. This limits their usefulness to patients with relatively strong pulses.

It should be noted that because changes in the settings of gains 44 and 48 and the digital input code transmitted to the DAC 50 can be changed every 1/240th of a second, the oximeter can readjust itself automatically by altering the gains 44 and 48 without losing any digital samples of the plethysmographic waveforms, and thus without interrupting the flow of information to the user.

Part of the readjustment is changing the amount of signal subtracted off by the DAC 50, that is, changing the digital input data. In general, this is necessary when gain 16, 44 or 48 is changed, but it is also required due to changes in the amount of light transmitted (see the description below of the processing of the digitized signal). The digital input code is altered to maintain the plethysmographic pulse within the range of the digitizer in the face of these slow changes.

To be able to determine the proper digital input code, it is necessary to use the following expressions. The first expression relates the digitized signal ("$V^*_{digitize}$") in terms of the voltage of the transmitted signal before gain 44 ("$V^*_{signal}$"), the two gains 44 and 48 and the voltage subtracted off of the signal by the DAC 50 ("$V^*_{subtract}$"):

$$V^*_{digitize} = [(V_{signal} \times \text{gain 44}) - V^*_{subtract}] \times \text{gain 48} \quad \text{(Equation 1)}$$

This can be rearranged to yield an expression for $V_{signal}$:

$$V_{signal} = [V^*_{subtract} + (V^*_{digitize}/\text{gain 48})]/\text{gain 44} \quad \text{(Equation 2)}$$

The following expression for $V^*_{subtract}$ is also useful:

$$V^*_{subtract} = (V_{signal} \times \text{gain 44}) - (V^*_{digitize})/\text{gain 48} \quad \text{(Equation 3)}$$

The asterisks in the terms $V^*_{subtract}$ and $V^*_{digitize}$ denote that these are values modified by one of eighteen pairs of values $V_{offset\text{-}digitizer}$ and $V_{offset\text{-}subtract}$ described in the previous section.

That is, $$V^*_{subtract} = V_{subtract} - V_{offset\text{-}subtract} \quad \text{(Equation 4)}$$

and $$V^*_{digitize} = V^*_{digitize} - V_{offset\text{-}digitize} \quad \text{(Equation 5)}$$

where $V_{subtract}$ is the actual value subtracted by the DAC 50 and $V_{digitize}$ is the actual value produced by the digitization section 24.

So equation (2) is used to reconstruct the size of the total signal at the input to gain 44 from its component parts. If we need to chanqe a gain, and wish to maintain the plethysmographic pulse in the same relative location within the digitization range, we use the third of the above equations to determine the new digital code for the DAC 50 to use to generate a signal to be subtracted from the outfit of gain 44.

To change a gain while maintaining the plethysmographic pulse in the same relative location within the digitization range, we use equation (3) to determine the new digital code for the DAC 50 to use to generate a signal to be subtracted from the output of gain 44. The value of $V_{signal}$ determined from equation (2) is used in evaluating equation (3), and the most recent digitized value is inserted as the value $V_{digitize}$ in the latter equation. Since successive samples are taken at a 120 Hz rate for each of the two channels (the red and the infrared), the physiological signal can be assumed to be constant over the period between the two successive samples.

Equation (3) is also used to determine a new digital code if we want to shift the plethysmographic pulse signal within the digitization range when slow changes in the transmitted level threaten to push the pulse outside of the range. In this case the amount by which we wish to shift the pulse is added to the most recent digitized value and inserted into $V_{digitize}$.

These expressions illustrate how the signal processing parameters of the circuitry can be altered between two successive digitized samples without affecting the coninuous operation of the device. As a result, the apparatus can respond to changes in signal size caused by changes in the physiological state of the patient in a manner transparent to the collection of data for further processing.

Gain 16, being before the low passed filters 40 and 42, cannot be altered without affecting continuous operation of the unit. The filters require about 25 to 30 ms to settle fully to the new voltage level, and thus a number of 240-Hz samples are lost. When this gain must be altered, the unit rejects the next few pulses while it determines from scratch the correct amount to be subtracted off by the DAC 50. The approach to finding the correct digital code for the DAC 50 is also used to lock onto the pulse initially, and involves a successive approximation routine similar to that used to perform the digitization period.

To reduce to an absolute minimum the required changes of gain 16, gains 16 and 44 are designed such that the combination of them exhibits hysteresis.

For example, referring to Table 2, consider a situation in which the transmitted intensity is steadily decreasing. Assume that the photocurrent is 5 mA and that the gains are #0 for gain 16 (with a resistance of, e.g., 500 kohms) and #2 for gain 44 ($\times 4$) for a composite transimpedance gain of 500 kohms. If the current drops off below 4 mA the gain changing strategy indicates that the gain drops to #1 for gain 16 (500 kohms) and #1 for gain 44 ($\times 2$), for a composite gain of 1 mA. Table 2 shows that if the photocurrent started rising again we could change gain 44 to a lower gain without incurring the delay associated with the filter response. In fact, the current would have to increase to more than 10 mA before it would be necessary to change gain 16.

This approach has an important advantage over, for example, the device of U.S. Pat. No. 4,407,290. In that device the hardware is continuously adjusting a variable gain to normalize the plethysmographic signal to a predetermined level. Consequently, the filters eguivalent to filters 40, 42 are continuously responding to changes in this variable gain, and one component of the total signal is an artifact of the electronic signal and not truly representative of what it is desired to measure.

In the approach of the present invention, the electronic gains are held constant before the filters 40, 42 so that the filters respond only to the true plethysmographic signal.

Processing of Signals by The Microprocessor Subsystem

To describe the processing of signals by the microprocessor subsystem, we start with the mathematical model of the absorption of light by the finger. As described above in the section on the background of the invention, we begin with Beer's Law for a spectrophotometric absorption process. Although this ideal law is only an approximation to the more complex physical situation, the acceptance of previous oximeters based upon this approximation indicates its usefulness.

$$V_R(t) = A_R K_R(t) \exp[-d(t)n(c_O \alpha_{OR} + (1-c_O)\alpha_{HR})] \quad \text{(Equation 6a)}$$

$$V_I(t) = A_I K_I(t) \exp[-d(t)n(c_O \alpha_{OI} + (1-c_O)\alpha_{HR})] \quad \text{(Equation 6b)}$$

$V_R(t)$ and $V_I(t)$ are the voltages generated by the detector and the signal processing circuitry for the red and infrared wavelengths respectively, and $d(t)$ represents the average path length through the arterial vascular bed that the incident light must travel to reach the detector; this path length increases when the volume of arterial blood in the finger increases;

$n$ represents the concentration of hemoglobin within that bed;

$c_O$ represents the fraction of oxyhemoglobin (%SaO$_2$);

$\alpha_O$ represents a characteristic absorption coefficient of oxyhemoglobin (one for red light, one for infrared);

$1-c_O$ represents the fraction of hemoglobin; and $\alpha_H$ represents a characteristic absorption coefficient of hemoglobin (one for red light, one for infrared).

Each signal has three components, as follows.

Very Slowly Changing Component (A)—Treating this as a constant component has an insignificant effect on the accuracy of the measurement. This component is a function of the illumination level, assorption by all the components of the finger except the blood, the detector sensitivity, and the gain of the signal processing circuitry.

Slowly Changing Component [K(t)]—This component represents the average amount of blood in the finger. During periods of unstable physiological conditions such as a change in the mean blood pressure or peripheral vascular resistance, the effect of this changing component must be included in the analysis.

Pulsatile Component $[\exp(-d(t)nc_O\alpha_O + (1-c_O)\alpha_H)]$—This is the component which is sensitive only to the characteristics of the arterial blood. The signal is caused by the changes in volume induced by the physiological pulse. Its size is dependent upon the %SaO$_2$.

The modeling of the slowly changing component, K(t), is one of the features which distinguish the present invention from conventional oximeters.

Since the pulsatile component modulates the full signal by a relatively small amount (typically, less than 10%), the complicated exponential can be reduced to its first order approximation.

$$\exp(-x) = 1 - x \text{ (for } x << 1\text{)}.$$

Then equations (6a) and (6b) are reduced to:

$$V_R(t) = A_R K_R(t)[1 - d(t)n(c_O \alpha_{OR} + (1-c_O)\alpha_{HR})] \quad \text{(Equation 7a)}$$

$$V_I(t) = A_I K_I(t)[1 - d(t)n(c_O \alpha_{OI} + (1-c_O)\alpha_{HI})] \quad \text{(Equation 7b)}$$

If we assume for the moment that the slowly changing components, $K_R(t)$ and $K_I(t)$, are constant then equations (6a) and (6b), can be rewritten:

$$\frac{A_R K_R - V_R(t)K}{A_R K_R} = d(t)n[c_O \alpha_{OR} + (1-c_O)\alpha_{HR}] \quad \text{(Equation 8a)}$$

$$\frac{A_I K_I - V_I(t)K}{A_I K_I} = d(t)n[c_O \alpha_{OI} + (1-c_O)\alpha_{HI}] \quad \text{(Equation 8b)}$$

It is convenient to choose two points separated in time from each of the red and infared signals, and subtract the right-hand sides of the equation (8a) and (8b) evaluated for the second point from the same expressions (8a) and (8b) evaluated for the first point.

This is illustrated by equations (9) and (10) written in a general form to apply to both the red and infrared signals.

$$\frac{AK - V(t_2)}{AK} - \frac{AK - V(t_1)}{AK} = d(t_2)n[c_O \alpha_O + (1-c_O)\alpha_H] - d(t_1)n[c_O \alpha_O + (1-c_O)\alpha_H] \quad \text{(Equation 9)}$$

$$\frac{V(t_2) - V(t_1)}{AK} = -[d(t_2) - d(t_1)]n[c_O \alpha_O + (1-c_O)\alpha_H] \quad \text{(Equation 10)}$$

Substituting the form of equation (10) back into equations (8a) and (8b), we arrive at equations (11a) and (11b)

$$\frac{V(t_2) - V(t_1)}{A_R K_R} = -[d(t_2) - d(t_1)]n[c_O \alpha_{OR} + (1-c_O)\alpha_{HR}] \quad \text{(Equation 11a)}$$

$$\frac{V(t_2) - V(t_1)}{A_I K_I} = -[d(t_2) - d(t_1)]n[c_O \alpha_{OI} + (1-c_O)\alpha_{HI}] \quad \text{(Equation 11b)}$$

Dividing equation (11a) by (11b) we get equation (12):

$$\frac{\frac{V_R(t_2) - V_R(t_1)}{A_R K_R}}{\frac{V_I(t_1) - V_I(t_1)}{A_I K_I}} = \frac{c_O \alpha_{OR} + (1-c_O)\alpha_{HR}}{c_O \alpha_{OR} + (1-c_O)\alpha_{HI}} \quad \text{(Equation 12)}$$

Equation (12) is based on the first order linear approximation for $\exp(-x)$. When the size of the physiological pulse becomes greater than 1% of the total signal (it can be as large as 10%) then it becomes necessary to calculate the second order term from the Taylor series approximation:

$$\exp(-x) = 1 - x + x^2/2$$

Using this approximation and neglecting higher-order terms, we find that equation (12) becomes $$\frac{\frac{V_R(t_2) - V_R(t_1)}{[V_R(t_2) + V_R(t_1)]/2}}{\frac{V_I(t_2) - V_I(t_1)}{[V_I(t_2) + V_2(t_1)]/2}} = \frac{c_0 \alpha_{OR} + (1 - c_0) \alpha_{HR}}{c_0 \alpha_{OI} + (1 - c_0) \alpha_{HI}} \quad \text{(Equation 12a)}$$

Thus, instead of the terms $A_R K_R$, $A_I K_I$ which represent the maximum values of the plethysmographic waveforms, we use $[V_R(t_2)+V_R(t_1)]/2$ and $[V_I(t_2)+V_I(t_1)]/2$, which represents the average level of the plethysmographic waveform at the time it is being analyzed.

Substituting the definition:

$$Z = \frac{\frac{V_R(t_2) - V_R(t_1)}{[V_R(t_2) + V_R(t_1)]/2}}{\frac{V_I(t_2) - V_I(t_1)}{[V_I(t_2) + V_I(t_1)]/2}} \quad \text{(Equation 13)}$$

into equation (12) and solving for $c_O$, we get equation (14):

$$c_0 = \frac{-(\alpha_{HR}) - Z(\alpha_{HI})}{(\alpha_{OR} + \alpha_{HI}) - Z(\alpha_{HI} - \alpha_{OI})} \quad \text{(Equation 14)}$$

Rather than solve equation (14) for $c_O$, which would involve many steps for microprocessor subsystem 26, a look up table is placed in the memory of microprocessor subsystem 26, which relates values for $c_O$ with the quotient Z.

The absorption characteristics may depend upon the body portion used. Thus, in the preferred embodiment, several look-up tables are provided, one table 27b for when the measurements are made using the patient's finger, one table 27b for when they are made using the earlobe, etc.

It should be noted that Z in equation (13) is a quotient of two individual quotients. The quotient in the numerator is associated with the red waveform and the quotient in the denominator is associated with the infrared waveform. Each of these individual quotients relates the change in the plethysmographic signal due to the physiological pulse (and the slowly varying component K(t)) to the average level of the two components.

If the two times $t_1$ and $t_2$ are chosen to correspond to the beginning of the systolic phase, when the voltage of the waveform is at a maximum, and the end of the systolic phase, when the voltage of the pulse is at a minimum, then the individual quotients would correspond directly to the percentage modulation. But in fact, since the shapes of the pulsatile components of the red and infrared signals both reflect the change in the volume of blood in the monitored area during the physiological pulse, and are therefore identical, we can choose any combination of voltage differences from any number of pairs of points as a measure of size, as long as we choose the identical combinations from corresponding pairs from the two waveforms. That is, we can use any arbitrary measure of the size of the pulse. Since the red and infrared data are digitized at alternate 1/240 second intervals, each piece of red data used in the calculations of size is actually the average of two consecutive values. Thus, interpolation estimates what the red value would have been if digitized simultaneously with the corresponding infrared velue, and points are taken from identical portions of the identically shaped waveforms.

The measure of size we choose to employ is preferably one which minimizes the electronic noise inherent in the various components of the oximeter 10. The preferred measure involves the use of multiple pairs of data points $V(t_1)$, $V(t_2)$ so that noise can be reduced by averaging contributions from these multiple pairs.

Figure 5:
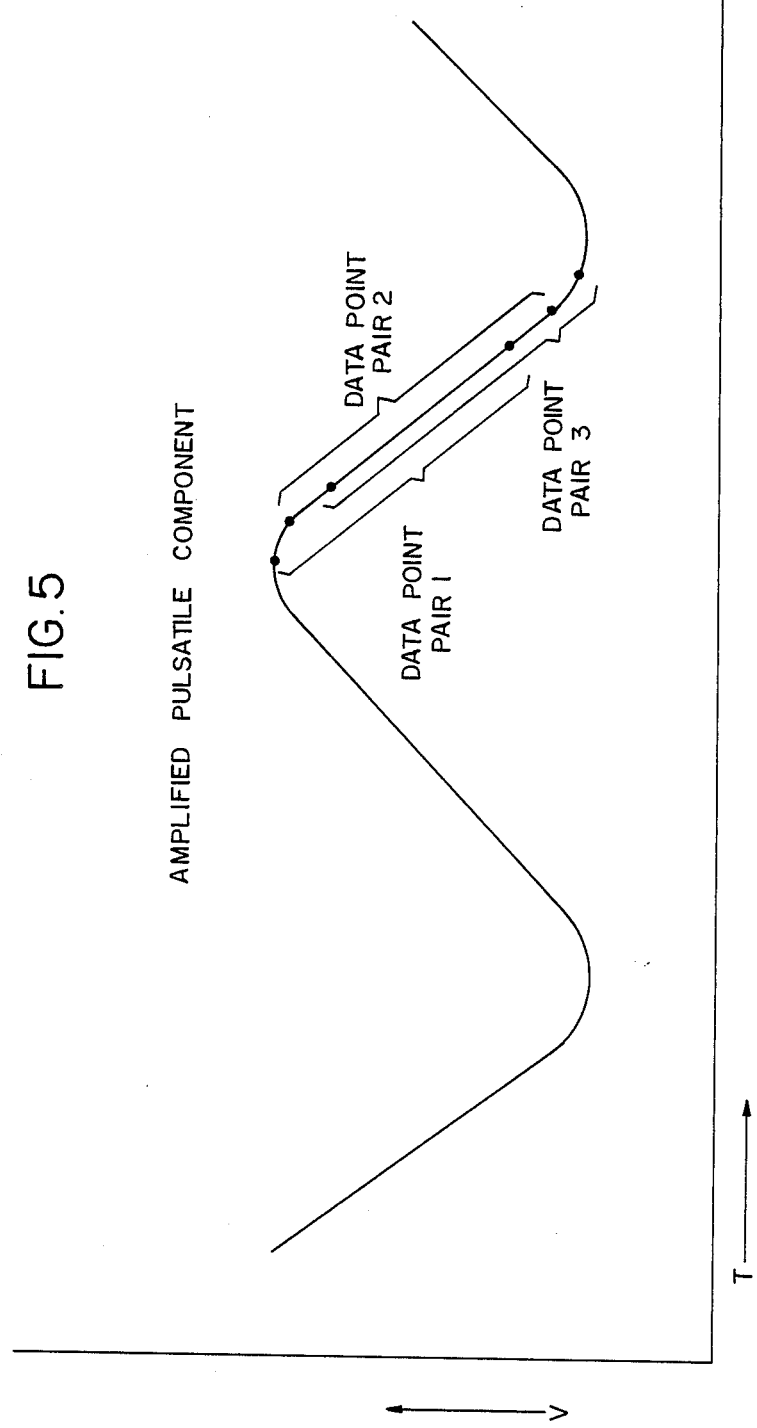
FIG. 5 is a schematic illustration of the method of compensating for electronic noise generated by the electrical components comprising the oximeter of the present invention.

The process is illustrated in FIG. 5, which shows an amplified version of how the voltage of the pulsatile component of the red waveform changes over time, with various voltages at different times identified by points on the waveform. Various points on the systolic portion of the waveform are paired up only with other points on the systolic portion of the waveform to produce pairs of points whose difference is greater than three-fourths of the full pulse size. In FIG. 5 the pairs satisfying this criterion are labeled data point pairs 1, 2, and 3. These pairs are used to compute the value of the pulsatile component of the red and infrared waveforms. In FIG. 5 the full pulse size represents the difference between the minimum and maximum values of the voltage of the red and infrared waveforms.

It should be noted that the points in these pairs are seguentially digitized points. Thus, the time difference associated with each pair is equal. The average of the voltage differences from the pairs from the red and infrared waveforms is used as the measure of the pulse size—that is, they are used for the two individual numerators in the expression for Z, from equation (13). In the same way, the average of the average values is used for the two denominators in the computation of Z.

Only those pairs of points whose voltage difference is greater than three-fourths of the full pulse height are used because the information provided by pairs of points whose difference is less than three-fourths of the full pulse height is outweighed by their contribution to noise. Pairs of points are only used from the systolic portion of the waveform because the rate of change of the signal is greater in that portion of the waveforms and thus the influence of slowly varying component K(t) described below is reduced.

A significant source of error arises when value of the voltage of the pulsatile component is not corrected for changes in slowly changing component K(t). K(t), which represents the average amount of blood in that portion of the body illuminated by LED's 34 and 36, as noted above, is not constant, but changes slowly. If K(t) is treated as a constant, a significant source of error is introduced into the computation of the oxygen saturation of the blood. This source of error occurs because a component of the computed size of the pulsatile signal will actually be due to the apparent drift of the pulse caused by the variation of K(t), as illustrated in FIG. 4. In order to compensate for this slowly changing component, a compensation algorithm is used by microprocessor subsystem 26 which assumes that the drift is linear from one pulse to the next. The algorithm permits microprocessor subsystem 26 to determine the approximate drift rate for each pair of pulses by subtracting the average of the maximum and minimum values of the voltages of the latter pulse in the pair of pulses (called the (n+1)st pulse) from the average of the maximum and minimum values for the voltages of the prior pulse in that same pair of pulses (called the nth pulse), and dividing this difference by the period of time between the minimum values of the (n+1)st pulse and the nth pulse. Because the size of each pulse is calculated from pairs of voltage differences, microprocessor subsystem 26 corrects the computed difference of each pair of voltages in the systolic portion of the (n+1)st pulse (that is, the pair of points on the waveform used earlier to compute the size of each pulse) by subtracting off from each of these differences, the product of the drift rate times the period of time elapsed between the points in each pair. However, because each pair has the same elapsed time between the two points in the pair, the product can be subtracted directly from the average value of the size computed above.

This process is illustrated in FIG. 4, which illustrates two pulses of either the red or infrared waveform, in which the voltage of the waveforms (the vertical axis) varies with time (the horizontal axis). As is clear from this figure, the systolic or left hand portion of each pulse is of shorter duration than the diastolic portion of each pulse. The voltage of the first or nth pulse, i.e. the pulse on the left, has an average level called the "last level" and the voltage of the second or (n+1)st pulse, i.e., the pulse on the right, has an average level called "level". Points on the upper half of the systolic portion of the second or (n+1)st pulse are labeled $x_1, x_2, x_3, x_4$, and $x_5$, and points on the lower half of the systolic portion of the second or (n+1)st pulse are labeled $y_1, y_2, y_3, y_4$, and $y_5$. In order to calculate the size of the second, or (n+1)st, pulse, points on the upper half and the lower half of the systolic portion of the second pulse are paired together so that the period of time elapsing between points in each pair are the same, i.e., $\Delta T$ is the same for each pair of points. More specifically, in order to calculate the size of the second or (n+1)st pulse, the difference between pairs of points are added and the resulting sum is divided by the number of pairs, i.e.:

$$\frac{(x_1 - y_1) + (x_2 - y_2) + (x_3 - y_3) + (x_4 - y_4) + (x_5 - y_5)}{5} \quad \text{(Expression 15)}$$

The drift experienced by the second pulse over interval $\Delta T$ is approximately:

$$\frac{(\text{last level} - \text{level})(\Delta T)}{\text{last pulse up} + \text{pulse down}} \quad \text{(Expression 16)}$$

where "last level" and "level" are the values of expression (13) for the nth and (n+1)st pulse, respectively, and where "last pulse up + pulse down" represents the elapsed time between the minimum value of the voltage of the first or nth pulse and the minimum value for the voltage of the second or (n+1)st pulse.

Microprocessor subsystem 26 compensates for the drift K(t) over time $\Delta T$ in the non pulsatile component by using the following modified version of expression (15) to determine the size of the pulse:

$$\frac{(x_1 - y_1) + (x_2 - y_2) + (x_3 - y_3) + (x_4 - y_4) + (x_5 - y_5)}{5} - \frac{(\text{last level} - \text{level})(\Delta T)}{\text{last pulse up} + \text{pulse down}} \quad \text{(Expression 17)}$$

It should be noted that although five pairs of points have been used in expressions (15) and (17), a larger or smaller number of points can be used. In this case, the denominator in expression (15) and that of the first term of expression (17) are the number of pairs of points that are present in the numerator. Further, in accordance with the noise correction discussed earlier, only those pairs which are such that the difference between the members of the pair is greater than three-fourths of the pulse height are to be used.

In addition, only points on the systolic portion of each pulse are used to compute the drift rate because, as noted above, the elapsed time between the points of the pairs on the systolic portion of each pulse is smaller than on the diastolic portion of each pulse. As a result, the errors due to imperfect compensation of the drift will be much smaller on the systolic portion of each pulse.

So finally, the algorithm used by the microprocessor subsystem to determine percent oxygen saturation uses modified versions of equations (13) and (14).

First, the quotient of Z is determined. As noted, Z is a quotient of two quotients, each of which is indicative of a percentage modulation of either a red or an infrared signal. Thus, we must make sure, in order to maintain the integrity of the individual quotients, that any scale factors applied to the numerator of each quotient is also applied to the denominator of each quotient. If we use the expression (17) to evaluate the numerators of the two individual quotients, we recognize that each data point in that expression has been multiplied by gains 16, 44 and 48. And if we use equation (2) to evaluate the individual denominators, we recognize that the result reflects a signal which has been multiplied by the value of gain 16 only. Therefore, to equalize the scale factors, we divide each of the numerators by the value of gain 48 and multiply each of the individual denominators by the value of gain 44. Thus, Z is evaluated as given by equation (18):

$$Z = \frac{\frac{(\text{Expression (17) for red})/(\text{gain 48})_{red}}{[V^*_{subtract}]_{red} + [V^*_{digitize,ave}]_{red}/(\text{gain 48})_{red}}}{\frac{(\text{Expression (17) for infrared})/(\text{gain 48})_{IR}}{[V^*_{subtract}]_{IR} + [V^*_{digitize,ave}]_{IR}/(\text{gain 48})_{IR}}} \quad \text{(Equation 18)}$$

where $V_{digitize,ave}$ is the average of the maximum digitized value of the pulse and the minimum digitized value of the pulse.

Finally, we use equation (14), which expresses the desired concentration, $c_O$, in terms of the signals detected and the constants $\alpha_{HR}$, $\alpha_{HI}$, $\alpha_{OR}$ and Z.

This correspondance can be calculated from the four characteristic absorptions and $\alpha_{OR}$, $\alpha_{OI}$, $\alpha_{HR}$ and $\alpha_{HI}$. These values are published for hemolyzed blood: that is, hemoglobin in solution without red blood cells.

However, in the case of the non invasive device of the present invention, the scattering of light from red blood cell interfaces, as well as the variability in vessel size and homogeneity and the hematocrit of the blood contained therein, perturb the effective coefficients. The best way to correlate the red/infrared ratio to the %SaO$_2$ is by empirical experiment on a large number of subjects whose %SaO$_2$ is determined by other methods.

It is beieved apparent, from the foregoing detailed description, that the functions of each of the blocks shown in FIG. 1 can be implemented readily by one of ordinary skill in the art after consideration of the disclosure herein.

Although the invention has been described with reference to particular means, methods, and embodiments, it should be understood that the invention is not limited thereto, but extends to all eguivalents within the scope of the claims.

TABLE 1

| GAIN 16 | | GAIN 44 | |
| --- | --- | --- | --- |
| Gain # | Transimpedance Gain | Gain # | Voltage Gain |
| (0) | 125 kΩ | (0) | × 1 |
| (1) | 500 kΩ | (1) | × 2 |
| (2) | 2 MΩ | (2) | × 4 |

TABLE 2

Composite Transimpedance Gain (Gain 16) × (Gain 44)
(For Preferable 2V–5V Output of Gain Stage 44)

| Photocurrent | (Gain 16#) | (Gain 44#) | Composite Transimpedance Gain | Gain Change |
| --- | --- | --- | --- | --- |
| 16 μA–>40 μA | (0) | (0) | 125 kΩ | |
| 8 μA–20 μA | (0) | (1) | 250 kΩ | |
| 4 μA–10 μA | (0) | (2) | 500 kΩ | |
| 4 μA–10 μA | (1) | (0) | 500 kΩ | |
| 2 μA–5 μA | (1) | (1) | 1 MΩ | |
| 1 μA–2.5 μA | (1) | (2) | 2 MΩ | |
| 1 μA–2.5 μA | (2) | (0) | 2 MΩ | |
| 0.50 μA–1.25 μA | (2) | (1) | 4 MΩ | |
| <0.25 μA–0.65 μA | (2) | (2) | 8 MΩ | |

TABLE 3

| | BEFORE | USE GAIN | | AFTER |
| --- | --- | --- | --- | --- |
| | <2 mV | (0) | × 100 | <200 mV |
| Preferable | 2 mV–20 mV | (0) | × 100 | 200 mV–2 V |
| Range | 8.9 mV–89 mV | (1) | × 22.4 | 200 mV–2 V |
| | 40 mV–500 mV | (2) | × 5 | 200 mV–2.5 V |
| | >500 mV | (2) | × 5 | >2.5 V |

Notes:
*Signal out of gain stage (44) is between 2V and 5V
*(0.1%)(2V) = 2 mV can be < plethysmographic signal before gain (48), which can be < (10%)(5V) = 500 mV
*200 mV should preferably be < plethysmographic signal after gain (48), which should preferably be < 2–2.5 V

What is claimed is:

1. A blood constituent measuring device for measuring a constituent of blood in a person's body, said device comprising:
   means for sensing electromagnetic energy passing through a portion of the body at a plurality of wavelengths and for producing, for each wavelength, a respective electrical signal comprising a pulsatile component and a non-pulsatile component, wherein said sensing and producing means produces each of the signals in response to the electromagnetic energy received at the respective wavelength;
   means for subtracting and storing at least a portion of the non pulsatile component from the signal for each wavelength;
   means for processing the pulsatile component of the signal for each wavelength and for computing the amount of the blood constituent as a function of the processed pulsatile component of each signal and the stored portion of the non pulsatile component of each signal; and
   means for amplifying, with a controllable gain, the pulsatile component of each signal after at least a portion of the non pulsatile component is subtracted from the respective signal, wherein said amplifying means amplifies the signals, after subtraction by said subtracting and storing means, to a sufficient extent that the amplified subtracted output signals are within a predetermined sensitivity range of said processing and computing means.

2. The device of claim 1, wherein said subtracting and storing means comprises a digital-to analog converter.

3. The device of claim 1, further comprising second amplifying means for amplifying the signals before said subtracting and storing means subtracts the portion of the non pulsatile components from the signals.

4. The device of claim 1, wherein said amplifying means amplifies with a controllable gain which is selected from among a plurality of predetermined values.

5. The device of claim 3, wherein each of said amplifying means amplifies with a respective controllable gain, each of said gains being selected, independently of each other, from among a respective plurality of predetermined values.

6. The device of claim 3, further comprising:
   electromagnetic energy emitting means for emitting electromagnetic energy at each of the wavelengths through the body portion seriatim, thereby to produce multiplexed electromagnetic energy and wherein said sensing and producing means comprises a photodetector for converting the electromagnetic energy transmitted through the body portion into analog electrical current signals and a current-to-voltage converter for converting the analog electrical current signals into analog voltage signals whose voltage varies with time;
   a demultiplexer for demultiplexing the signals produced by said current to voltage converter so as to produce two separate signals in first and second channels, respectively, representing electromagnetic energy of different wavelengths from said electromagnetic energy emitting means passing through the body portion;
   two low pass filters, each connected to said demultiplexer through a respective one of said channels, wherein each said filter receives a respective one of the two separate signals; and
   a remultiplexer connected to both channels for remultiplexing the two separat signals after filtering by said filters, wherein the output from said multiplexer is received by said means for amplifying the signals before subtraction of a portion of the non-pulsatile component; and
   wherein said digital to analog converter also converts the pulsatile component of the demultiplexed, subtracted and amplified signals into digital output signals.

7. The device of claim 6, wherein said filters are frequency-matched to each other.

8. The device of claim 6, further comprising a sequencer for controlling said current-to voltage converter, and wherein said processing and computing means comprises a microprocessor subsystem, distinct and separate from said sequencer, which microprocessor subsystem controls said sequencer.

9. The device of claim 6, further comprising means for preventing an electrosurgical unit being used on the body from interfering with the operation of said photodetector, wherein said interference preventing means comprises a partially transparent window, to be positioned between said photodetector and the body portion.

10. The device of claim 6, wherein said electromagnetic energy emitting means comprises first and second emitters for emitting electromagnetic energy at a first of said wavelengths and a third emitter for emitting electromagnetic radiation at a second of said wavelengths, said third emitter being disposed generally between said first and second emitters, and said three emitters being disposed sufficiently close together to ensure that the body portion through which the radiation that is sensed by said sensing means passes, receives on the average substantially equal luminance due to the energy at said first and second wavelengths.

11. The device of claim 1, further comprising means for digitizing the subtracted portion of the non pulsatile component of the signals and for computing the instantaneous value of the non pulsatile component of the signals.

12. The device of claim 11, further comprising means for digitizing the pulsatile component after the portion of the non-pulsatile component is subtracted from the signals, wherein said amplifying means amplifies the pulsatile component before digitization by the digitization means, and wherein said amplifying means amplifies the pulsatile component sufficiently that the digitized pulsatile component has a height of at least fifty times the resolution of said digitizing means.

13. The device of claim 1, wherein the portion of the non-pulsatile component varies with time in such a manner as to change the value of the pulsatile component, and wherein said processing and computing means comprises means for compensating for the change in the value of the pulsatile component due to the varying of the non pulsatile component.

14. The device of claim 13, wherein the pulsatile component comprises first and second pulses, wherein the non pulsatile component causes the pulsatile component to vary at a drift rate, and wherein said compensation means comprises means for calculating the drift rate by the following formula:

$$[(\tfrac{1}{2})(Max+Min)_1 - (\tfrac{1}{2})(Max+Min)_2]/\Delta T$$

wherein $(Max+Min)_1$ represents the sum of the maximum value and minimum value of the voltage of the first pulse, $(Max+Min)_2$ represents the sum of the maximum value and the minimum value of the voltage of the second pulse, and wherein $\Delta T$ represents the time elapsed between the minimum values of the voltages of said first and second pulses.

15. The device of claim 13, wherein the pulsatile component comprises a plurality of pairs of pulses, wherein said compensation means comprises means for calculating the drift rate for each pair of pulses by the following formula:

$$[(\tfrac{1}{2})(Max+Min)_n - (\tfrac{1}{2})(Max+Min)_{n+1}]/\Delta T$$

wherein $(Max+Min)_n$ represents the sum of the maximum value and minimum value of the voltage of the nth pulse of the pulsatile component, wherein $(Max+Min)_{n+1}$ represents the sum of the maximum value and the minimum value of the voltage of the $(n+1)$st pulse of the pulsatile component, the $(n+1)$st pulse occurring later in time than the nth pulse, wherein $\Delta T$ represents the time elapsed between the minimum values of the voltages of the nth and $(n+1)$st pulses, and wherein n assumes the value of each of a predetermined set of positive integers.

16. The device of claim 15, wherein said compensation means further comprises means for subtracting the product of the drift rate and the duration of the nth pulse from the average value of the voltage of the $(n+1)$st pulse.

17. The device of claim 16, wherein said compensation means computes the average value of the voltage of the $(n+1)$st pulse only during the systolic portion of the $(n+1)$st pulse.

18. The device of claim 16, wherein said compensation means computes the average value of the voltage of the $(n+1)$st pulse by adding pairs of values for the voltage of the $(n+1)$st pulse, which pairs are selected such that the difference between the values of the pair is greater than three-fourths of the difference between the maximum and minimum values of the voltage of the $(n+1)$st pulse, and dividing the resulting sum by the number of such pairs.

19. The device of claim 1, further comprising electromagnetic energy emitting means for alternately emitting red and infrared wavelengths of light, wherein said processing and computing means comprises means for computing the percentage of oxygen saturation of hemoglobin in the blood of the body.

20. The device of claim 19, wherein said processing and computing means comprises means for computing said percentage of oxygen saturation by dividing a first quotient:

$$\frac{[\text{voltage of pulsatile component of the red wavelength}]}{[\text{voltage of non-pulsatile component of the red wavelength}]}$$

by a second quotient:

$$\frac{[\text{voltage of pulsatile component of the infrared wavelength}]}{[\text{voltage of non-pulse component of the infrared wavelength}]}.$$

21. The device of claim 20, wherein the pulsatile component comprises a plurality of pulses, each corresponding to a pulse of the blood of the body, wherein each pulse of the pulsatile component has a voltage varying over time, and wherein said computing means computes the value of the voltage of each pulse of the pulsatile component of the red wavelength by computing, for each of a plurality of pairs of values for the voltage of one pulse wherein the difference between the values of the pair is greater than three-fourths of the difference between the maximum and minimum value of the voltage of that pulse, the quotient of their difference divided by the number of such pairs, and repeating said computing step for each pulse.

22. The device of claim 20, wherein said means for computing said percentage of oxygen saturation includes at least one look-up table for looking up said percentage of oxygen saturation as a function of the quantity obtained by dividing said first quotient by said second quotient.

23. The device of claim 22, wherein said means for computing said percentage of oxygen saturation includes at least two such look-up tables, each of said look-up tables being for use in connection with the electromagnetic energy being passed through a different respective body portion.

24. The device of claim 23, wherein one of said look-up tables is suitable for use in a case in which the electromagnetic radiation is passed through an ear lobe, and a second of said look-up tables is suitable for use in a case in which the electromagnetic reduction is passed through a finger.

25. A blood constituent measuring device for measuring at least one constituent of blood in a body, comprising:
    means for sensing electromagnetic energy passing through a portion of the body at a plurality of wavelengths and for producing electrical signals comprising a pulsatile component and a non pulsatile component for each wavelength in response to the electromagnetic energy received by said sensing and producing means at a plurality of wavelengths, wherein the electrical signals comprise voltage signals whose voltage varies over time, and wherein the voltage of the non-pulsatile component varies over time in such a manner as to change the value of the voltage of the pulsatile component over time; and means for processing the pulsatile component of the signals for each wavelength and for computing the amount of the blood constituent as a function of the processed pulsatile component and the non pulsatile component of the output signals, wherein said processing and computing means further comprises means for compensating for the change in the value of the voltage of the pulsatile component over time due to the varying of the voltage of the non pulsatile component over time.

26. The device of claim 25, wherein the non-pulsatile component varies in such a manner as to change the value of the pulsatile component linearly; and said device further comprising means for compensating for the linear change in the value of the pulsatile component due to the varying of the non-pulsatile component.

27. The device of claim 26, wherein the pulsatile component comprises first and second pulses, wherein the non-pulsatile component varies the value of the voltage of the pulsatile component over time at a predetermined drift rate, wherein said compensation means comprises means for calculating the drift rate by the following formula:

$$[(\tfrac{1}{2})(Max+Min)_1 (\tfrac{1}{2})(Max+Min)_2]/\Delta T$$

wherein $(Max+Min)_1$ represents the sum of the maximum value and minimum value of the voltage of the first pulse of the pulsatile component, $(Max+Min)_2$ represents the sum of the maximum value and the minimum value of the voltage of said second pulse of the pulsatile component, and $\Delta T$ represents the time elapsed between the minimum values of the voltage of the first and second pulses.

28. The device of claim 26, wherein the pulsatile component comprises a plurality of pairs of pulses, wherein said compensation means comprises means for calculating the drift rate for each pair of pulses by the following formula:

$$[(\tfrac{1}{2})(Max+Min)_n - (\tfrac{1}{2})(Max+Min)_{n+1}]/\Delta T$$

wherein $(Max+Min)_n$ represents the sum of the maximum value and minimum value of the voltage of the nth pulse of the pulsatile component, $(Max+Min)_{n+1}$ represents the sum of the maximum value and the minimum value of the voltage of the (n+1)st pulse of the pulsatile component, wherein the (n+1)st pulse occurs later in time than the nth pulse, and wherein $\Delta T$ represents the time elapsed between the minimum values of the voltage of the nth and (n+1)st pulses, and wherein n is assumes the value of each of a plurality of positive integers.

29. The device of claim 28, wherein said compensation means further comprises means for correcting the (n+1)st pulse of the pulsatile component by subtracting the product of the drift rate and the duration of nth pulse from the average value of the voltage of the (n+1)st pulse.

30. The device of claim 29, wherein said compensation means computes the value of the voltage of the (n+1)st pulse of the pulsatile component only during the systolic portion of the pulse.

31. The device of claim 29, wherein said computing means computes the average value of the voltage of the (n+1)st pulse of the pulsatile component by computing, for each of a plurality of pairs of values for the voltage of the (n+1)st pulse such that the difference between the values of the members of a pair is greater than three quarters of the difference between the maximum and minimum values of the voltage of the (n+1)st pulse, the quotient of that difference divided by the number of such pairs.

32. The device of claim 25, wherein said processing and computing means includes a plurality of look-up tables which are respectively for looking up the blood constituent amount as a function of the signals, each of said look-up tables being for use in connection with the electromagnetic energy being passed through a different respective body portion.

33. A blood constituent measuring device for measuring a constituent of blood in a person's body, said device comprising:

means for sensing electromagnetic energy passing through a portion of the body at a plurality of wavelengths and for producing, for each wavelength, a respective electrical signal comprising a pulsatile component and a non-pulsatile component, wherein said sensing and producing means produces each of the signals in response to the electromagnetic energy received at the respective wavelength;

means for filtering the signals;

means for subtracting and storing at least a portion of the non-pulsatile component from the filtered signal for each wavelength;

means for processing the pulsatile component of the signal for each wavelength and for computing the amount of the blood constituent as a function of the processed pulsatile component of each signal and the stored portion of the non-pulsatile component of each signal; and at least two means for amplifying the signals to a sufficient extent that the amplified subtracted output signals are within a predetermined sensitivity range of said processing and computing means, each of said amplifying means having a gain controllable independently of that of the other.

34. The device of claim 33, wherein each said amplifying means amplifies the signal for each wavelength, and each of said amplifying means has its gain controlled independently for each wavelength.

35. The device of claim 33, wherein one of said amplifying means amplifies the signals after said subtracting and storing means has subtracted the portion of the non-pulsatile component of each signal.

36. A blood constituent measuring device for measuring a constituent of blood in a person's body, said device comprising:

means for emitting electromagnetic energy at a plurality of wavelengths, said emitting means comprising a first emitter for emitting energy at a first of said wavelengths, and second and third emitters for emitting energy at a second of said wavelengths, said second and third emitters being disposed one to each side of said first emitter such that, on the average, substantially equal luminance due to the energy at the first and second wavelengths is incident on a body portion at a predetermined position relative to said emitting means;

means for sensing electromagnetic energy from said emitting means and passing through a portion of the body and for producing, for each wavelength, a respective electrical signal comprising a pulsatile component and a non-pulsatile component, wherein said sensing and producing means produces each of the signals in response to the electromagnetic energy received at the respective wavelength; and means for processing the pulsatile component of the signal for each wavelength and for computing the amount of the blood constituent as a function of the pulsatile component of each signal.

37. A blood constituent measuring device for measuring a constituent of blood in a person's body, said device comprising:

electromagnetic energy emitting means operable in a monitoring mode and in a test mode, wherein, in said monitoring mode, said electromagnetic energy emitting means emits electromagnetic energy at each of N wavelengths (N an integer greater than 1) seriatim through a portion of the body during a predetermined period of time, thereby to produce multiplexed electromagnetic energy passing through the body portion; and wherein, in said test mode, said electromagnetic energy emitting means emits electromagnetic energy at only one of said wavelengths;

means for sensing the electromagnetic energy passing through the body portion and for producing during said predetemined period of time during operation in said monitoring mode, a respective electrical signal corresponding to each of said N wavelengths, wherein said sensing and producing means produces each of the signals in response to the electromagnetic energy received at the respective wavelength; and said sensing and producing means producing, during said predetermined period of time during operation in said test mode, N electrical signals in response to the electromagnetic energy received at said one wavelength; wherein each of the signals comprises a pulsatile component and a non-pulsatile components in both modes;

means for processing the pulsatile component of each signal and for computing the amount of the blood constituent as a function of the processed pulsatile component of each signal; and means for controlling said electromagnetic energy emitting means to operate selectively in said monitoring mode or in said test mode, wherein said processing means is so structured and arranged that, when said electromagnetic energy emitting means operates in said test mode, the amount computed by said processing means is compared to a predetermined value.

38. A method of determining the amount of at least one constituent of the blood in a person s body, comprising the steps of:

sensing a plurality of wavelengths of electromagnetic radiation passing through a portion of the body, with a sensing means;

producing voltage signals corresponding to the electromagnetic radiation sensed in said sensing step, the voltage of each signal varying with time, and wherein the voltage signals each comprise a pulsatile component and a non-pulsatile component;

subtracting and storing at least a portion of the non-pulsatile component from each voltage signal;

processing the pulsatile component of each voltage signal and computing the amount of the blood constituent as a function of the processed pulsatile components and the stored portion of the non-pulsatile components; and amplifying the pulsatile components after at least a portion of the non pulsatile components is subtracted from the voltage signals.

39. The method of claim 38, wherein said producing step further comprises producing analog electrical signals, and wherein said subtraction step further comprises digitally subtracting and storing at least a portion of the non-pulsatile component of each of the voltage signals.

40. The method of claim 38, further comprising the step of adding a predetermined negative voltage to the voltage signals before said subtraction and storage step.

41. The method of claim 38, further comprising the step of amplifying the signals before said subtraction step and after said producing step.

42. The method of claim 39, further comprising the steps of:

emitting and transmitting electromagnetic energy at a plurality of predetermined wavelengths through the body portion seriatim to produce multiplexed electromagnetic energy transmitted through the body;

converting the multiplexed electromagnetic energy transmitted through the body portion into analog electrical current signals with a photodetector and converting the current signals into the voltage signals with a current-to-voltage converter;

demultiplexing the voltage signals so as to produce two separate signals in first and second channels representing electromagnetic energy passing through the body portion at different wavelengths;

low-pass filtering the separate signals in the first and second channels, using low pass filters connected to the demultiplexer through respective channels;

remultiplexing the two separate signals after said filtering step; and amplifying the signals after said remultiplexing step and before said subtraction step.

43. The method of claim 42, further comprising the step of digitizing the pulsatile component of the analog voltage signals after said subtraction step.

44. The method of claim 43, further comprising the step of amplifying the pulsatile component before said digitization step and after said subtraction step, sufficiently that the digitized pulsatile component has a resolution of at least eight bits.

45. The method of claim 38, wherein the non-pulsatile component varies in such a manner as to change the value of the voltage of the pulsatile component, and further comprising the step of compensating for the change in the value of the voltage of the pulsatile component due to the varying of the non pulsatile component.

46. The method of claim 45, wherein the pulsatile component comprises first and second pulses, wherein the non-pulsatile component causes the average voltage of the pulsatile component to vary at a predetermined drift rate, and wherein said compensation step comprises the step of calculating the drift rate by the following formula:

$$[(\tfrac{1}{2})(Max+Min)_1-(\tfrac{1}{2})(Max+Min)_2]/\Delta T$$

wherein $(Max+Min)_1$ represents the sum of the maximum value and minimum value of the voltage of the first pulse of the pulsatile component, $(Max+Min)_2$ represents the sum of the maximum value and the minimum value of the voltage of the second pulse of the pulsatile component, and $\Delta T$ represents the time elapsed between the minimum values of the voltages of the first and second pulses.

47. The method of claim 45, wherein the pulsatile componet comprises a plurality of pairs of pulses, wherein said compensation step further comprises the step of calculating the drift rate for each aair of pulses by the following formula:

$$[(\tfrac{1}{2})(Max+Min)_n-(\tfrac{1}{2})(Max+Min)_{n+1}]/\Delta T$$

wherein $(Max+Min)_n$ represents the sum of the maximum value and minimum value of the voltage of the nth pulse of the pulsatile component, $(Max+Min)_{n+1}$ represents the sum of the maximum value and the minimum value of the voltage of the (n+1)st pulse of the pulsatile component, wherein the (n+1)st pulse occurs later in time than the nth pulse, and $\Delta T$ represents the time elapsed between said minimum values of the voltages of of said nth and (n+1)st pulses, and wherein n assumes the values of each of a plurality of positive integers.

48. The method of claim 47, wherein said compensation step further comprises the step of correcting the (n+1)st pulse of the pulsatile component by subtracting the product of the drift rate and the duration of the nth pulse from the average value of the voltage of the (n+1)st pulse.

49. The method of claim 48, wherein said compensation step further comprises the step of computing the value of the voltage of the (n+1)st pulse only during the systolic portion of the pulse.

50. The method of claim 49, wherein said compensation step further comprises the step of computing the average value of the voltage of the (n+1)st pulse by computing, for each of a plurality of pairs of values for the voltage of the (n+1)st pulse which pairs are such that the difference between the members of the pair is greater than three quarters of the difference between the maximum and minimum values of the voltage of the (n+1)st pulse, the quotient of their difference divided by the number of such pairs.

51. The method of claim 38, further comprising the step of alternately emitting red and infrared wavelengths of light and transmitting the red and infrared wavelengths of light through the body portion, and wherein said processing and computing steps further comprise the step of computing the percentage of oxygen saturation in the blood of the body.

52. The method of claim 51, wherein said processing and computing steps further comprise the step of computing the percentage of oxygen saturation by dividing a first quotient:

$$\frac{[\text{voltage of pulsatile component of the red wavelength}]}{[\text{voltage of non-pulsatile component of the red wavelength}]}$$

by a second quotient:

$$\frac{[\text{voltage of pulsatile component of the infrared wavelength}]}{[\text{voltage of non-pulse. component of the infrared wavelength}]}$$

53. The method of claim 52, wherein the pulsatile component comprises a plurality of pulses, each corresponding to a pulse of the blood in the body, wherein each pulse of the pulsatile component has a voltage varying over time; and wherein said computing step further comprises the step of computing the value of the voltage of each pulse of the pulsatile component of the red wavelength signal by computing, for each of a plurality of pairs of values for the voltage of one pulse such that the difference between the members of one pair is greater than three quarters of the difference between the maximum and minimum values of the voltage of that one pulse, the quotient of their difference by the number of pairs of values, and repeating said computing step for each pulse.

54. The method of claim 52, wherein said step of computing the percentage of oxygen saturation comprises looking up values of oxygen saturation in a look-up table based on the quotient of said first and second quotients.

55. A method for measuring at least one constituent of the blood in a body, comprising the steps of:
sensing electromagnetic energy passing through a portion of the body at a plurality of wavelengths;
producing electrical signals comprising a pulsatile component and a non-pulsatile component for each wavelength in response to said sensing of the electromagnetic energy, wherein the voltage of the signals varies over time, and wherein the voltage of the non-pulsatile component varies over time in such a manner as to cause the average value of the voltage of the pulsatile component to change over time; and
processing the pulsatile component of the output signals for each wavelength and computing the amount of the blood constituent as a function of the processed pulsatile component and the non-pulsatile component, wherein said processing and computing step further comprises the step of compensating for the change in the value of the voltage of the pulsatile component over time due to the varying of the non-pulsatile component over time.

56. The method of claim 55, wherein the pulsatile component comprises first and second pulses, wherein the non-pulsatile component varies the value of the average voltage of the pulsatile component over time at a predetermined drift rate, and wherein said compensation step comprises the step of calculating the drift rate by the following formula:

$$[(\tfrac{1}{2})(Max+Min)_1-(\tfrac{1}{2})(Max+Min)_2]/\Delta T$$

wherein $(Max+Min)_1$ represents the sum of the maximum value and minimum value of the voltage of the first pulse of the pulsatile component, $(Max+Min)_2$ represents the sum of the maximum value and the minimum value of the voltage of the second pulse of said pulsatile component, and $\Delta T$ represents the time elapsed between said minimum values of the voltage of the first and second pulses.

57. The method of claim 55, wherein the pulsatile component comprises a plurality of pairs of pulses, wherein said compensation step further comprises the step of calculating the drift rate for each pair of pulses by the following formula:

$$[(\tfrac{1}{2})(Max+Min)_n - (\tfrac{1}{2})(Max+Min)_{n+1}]/\Delta T$$

where $(Max+Min)_n$ represents the sum of the maximum value and minimum value of the voltage of the nth pulse of the pulsatile component, $(Max+Min)_{n+1}$ represents the sum of the maximum value and the minimum value of the voltage of the (n+1)st pulse of the pulsatile component, where said (n+1)st pulse oocurs later in time than said nth pulse, and $\Delta T$ represents the time elapsed between said minimum values of the voltage of the nth and (n+1)st pulses, wherein n takes on the value of each of a set of positive integers.

58. The method of claim 57, wherein said compensation step further comprises the step of correcting the (n+1)st pulse of the pulsatile component by subtracting the product of the drift rate and the duration of the nth pulse from the average value of the voltage of the (n+1)st pulse.

59. The method of claim 58, wherein said compensation step further comprises the step of computing the average value of the voltage of the (n+1)st pulse only during the systolic portion of the (n+1)st pulse.

60. The method of claim 58, wherein said compensation step further comprises the step of computing the average value of the voltage of the (n+1)st pulse by computing, for each of a plurality of pairs of values for the voltage of the (n+1)st pulse such that the difference between the members of a pair is greater than three quarters of the difference between the maximum and minimum values of the voltage of the (n+1)st pulse, the quotient of their difference divided by the number of such pairs.

* * * * *